United States Patent
Swager et al.

(10) Patent No.: US 12,247,945 B2
(45) Date of Patent: Mar. 11, 2025

(54) SENSORS INCLUDING REDOX-ACTIVE SELECTOR COMPLEXES

(71) Applicants: MASSACHUSETTS INSTITUTE OF TECHNOLOGY, Cambridge, MA (US); KING ABDULLAH UNIVERSITY OF SCIENCE AND TECHNOLOGY, Thuwal (SA)

(72) Inventors: Timothy M. Swager, Newton, MA (US); Suchol Savagatrup, Cambridge, MA (US); Vera Schroder, Cambridge, MA (US); Maggie He, Cambridge, MA (US); Sibo Lin, Cambridge, MA (US); Xi-Xiang Zhang, Thuwal (SA); Khaled N. Salama, Thuwal (SA)

(73) Assignees: Massachusetts Institute of Technology, Cambridge, MA (US); King Abdullah University of Science and Technology, Thuwal (SA)

(*) Notice: Subject to any disclaimer, the term of this patent is extended or adjusted under 35 U.S.C. 154(b) by 0 days.

(21) Appl. No.: 16/132,336

(22) Filed: Sep. 14, 2018

(65) Prior Publication Data
US 2019/0086360 A1  Mar. 21, 2019

Related U.S. Application Data

(60) Provisional application No. 62/560,186, filed on Sep. 18, 2017.

(51) Int. Cl.
*G01N 27/414* (2006.01)
*G01N 27/30* (2006.01)
*G01N 27/48* (2006.01)
*G01N 33/00* (2006.01)

(52) U.S. Cl.
CPC ....... *G01N 27/4141* (2013.01); *G01N 27/308* (2013.01); *G01N 27/4146* (2013.01); *G01N 27/48* (2013.01); *G01N 33/004* (2013.01)

(58) Field of Classification Search
CPC ........ B65D 65/40; C08G 18/40; C09J 175/04; G01N 27/4141; G01N 27/308; G01N 27/4146; G01N 27/48; G01N 33/004
See application file for complete search history.

(56) References Cited

U.S. PATENT DOCUMENTS

| 6,323,309 B1 | 11/2001 | Swager |
| 6,328,932 B1 | 12/2001 | Carter |
| 8,623,281 B2 | 1/2014 | Setayesh |
| 2007/0235773 A1 | 10/2007 | Eisele |

(Continued)

FOREIGN PATENT DOCUMENTS

| IN | 1923/MUM/2012 | * | 1/2014 |
| WO | WO-2017137086 A1 | * | 8/2017 |

OTHER PUBLICATIONS

S. Badhulika, et al., Conducting polymer coated single-walled carbon nanotube gas sensorsfor the detection of volatile organic compounds, Talanta, vol. 123, pp. 109-114 (2014) (Year: 2014).*

(Continued)

*Primary Examiner* — J. Christopher Ball
(74) *Attorney, Agent, or Firm* — Wolf, Greenfield & Sacks, P.C.

(57) ABSTRACT

A sensor can include a redox-active complex. The sensor can be voltage sensitive.

20 Claims, 38 Drawing Sheets

(56) References Cited

U.S. PATENT DOCUMENTS

| | | | | |
|---|---|---|---|---|
| 2009/0014757 | A1* | 1/2009 | Takulapalli | G01N 27/4145 257/253 |
| 2011/0239735 | A1 | 10/2011 | Setayesh | |
| 2013/0273665 | A1* | 10/2013 | Swager | G01N 27/125 436/142 |
| 2016/0290980 | A1* | 10/2016 | Swager | G01N 33/0054 |

OTHER PUBLICATIONS

A.D. Rushi, et al., Selective Discrimination among Benzene, Toluene, and Xylene: Probing Metalloporphyrin-Functionalized Single-Walled Carbon Nanotube-Based Field Effect Transistors, J. Phys. Chem. C, vol. 118, No. 41, pp. 24034-24041 (2014) (Year: 2014).*

M. Alvaro, et al., Synthesis, Photochemistry, and Electrochemistry of Single-Wall Carbon Nanotubes with Pendent Pyridyl Groups and of Their Metal Complexes with Zinc Porphyrin. Comparison with Pyridyl-Bearing Fullerene, J. Am. Chem. Soc., vol. 128, pp. 6626-6635 (2006) (Year: 2006).*

E.S. Snow, et al., "Random network of carbon nanotubes as an electronic material", Applied Physics Letters, 82(13): p. 2145-2147, Mar. 2003.*

M. Penza, et al., "Metalloporphyrins-modified carbon nanotube networked films-based chemical sensors for enhanced gas sensitivity", Sensor and Actuators B: Chemical, 144(2): p. 387-394, Feb. 2010.*

Alvarez et al, 'Redox Potential Determines the Reaction Mechanism of HNO Donors with Mn and Fe Porphyrins: Defining the Better Traps', Inorganic Chemistry, vol. 53, Jul. 8, 2014, p. 7351-7360.

Dong et al, 'Heme-Enabled Electrical Detection of Carbon MonoKIde at Room Temperature Using Networked Carbon Nanotube Field-Effect Transistors', Chemistry of Materials, vol. 19 Issue 25, Dec. 11, 2007, p. 6059-6061.

Piantadosi, 'Carbon Monoxide, Reactive Oxygen Signaling, and Oxidative Stress', PubMed Central Author Manuscripts, article No. PMC2570053, Sep. 1, 2009, p. 1-21, [retrieved Mar. 12, 2019 (Mar. 12, 2019) via the internet at <https:llwww.ncbi.nlm.nih.gov/pmc/articles/PMC2570053J>].

Savagatrup et al, 'Bio-Inspired Carbon Monoxide Sensors with Voltage-Activated Sensitivity', Angewandte Chemie International Edition, vol. 56, Sep. 26, 2017, p. 14066-14070.

International Search Report and Written Opinion from PCT/US2018/51247, mailed Mar. 27, 2019.

Notification Concerning Transmittal of International Preliminary Report on Patentability for PCT/US2018/051247 mailed Apr. 2, 2020.

* cited by examiner

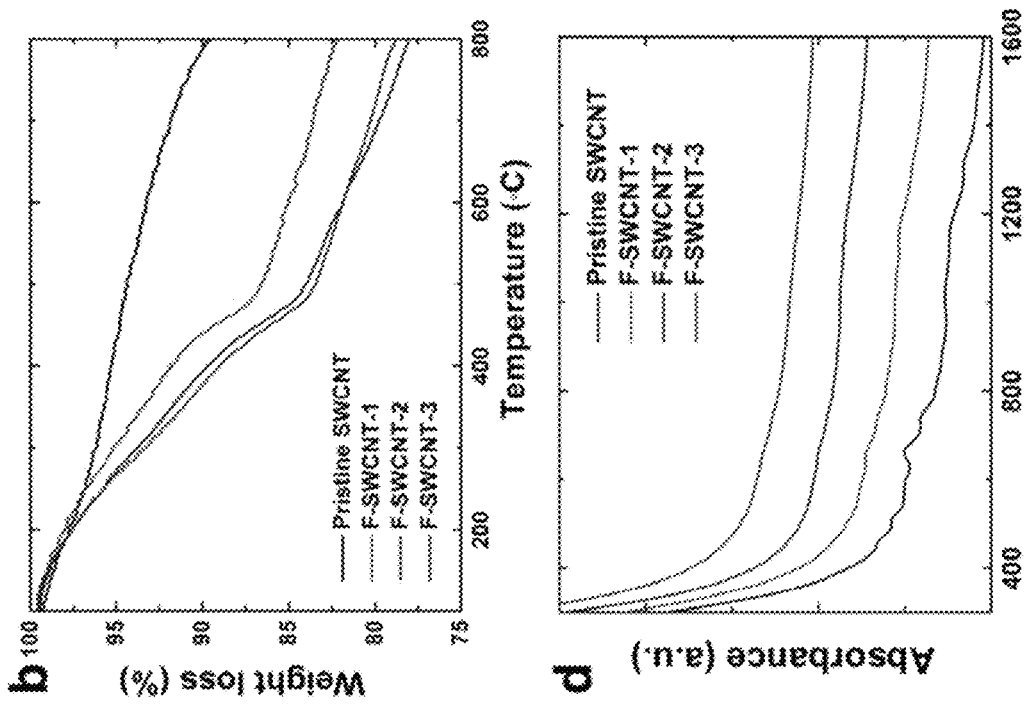
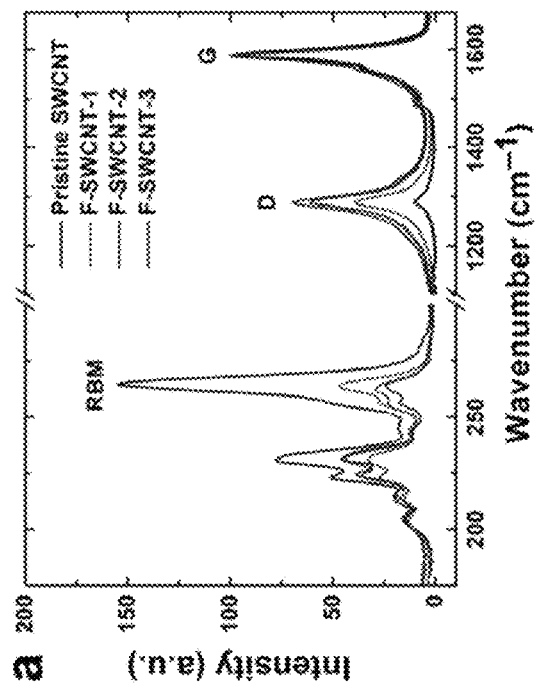
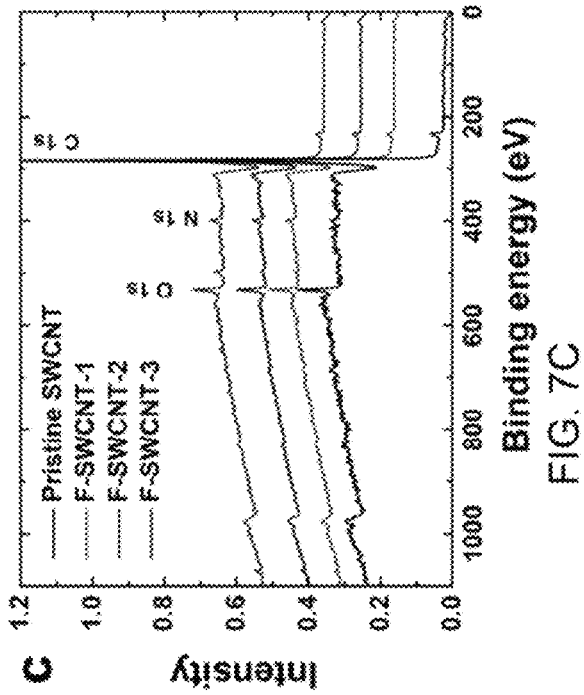
FIG. 7A  FIG. 7B  FIG. 7C  FIG. 7D

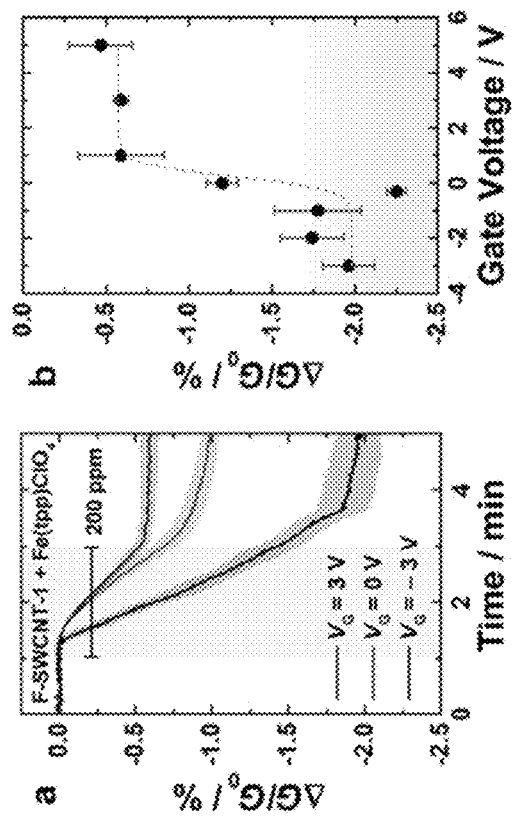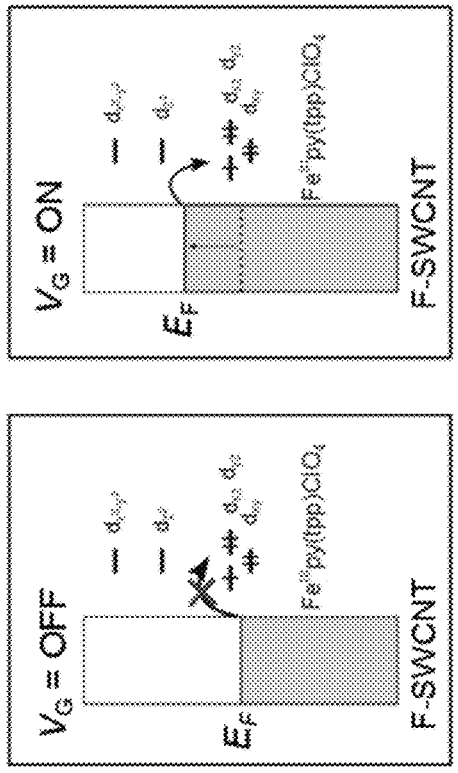
FIG. 11A  FIG. 11B  FIG. 11C

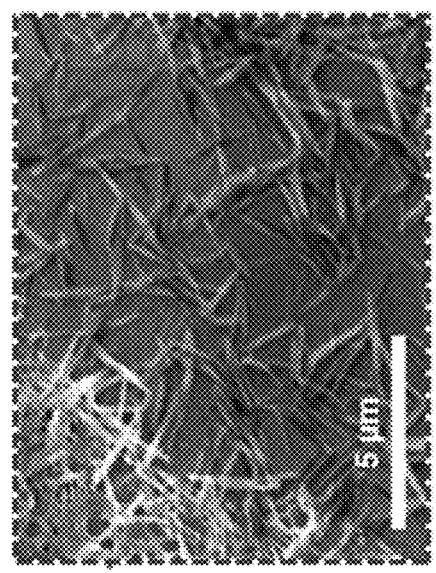
FIG. 16A Mixed F-SWCNTs:Fe(tpp)ClO$_4$
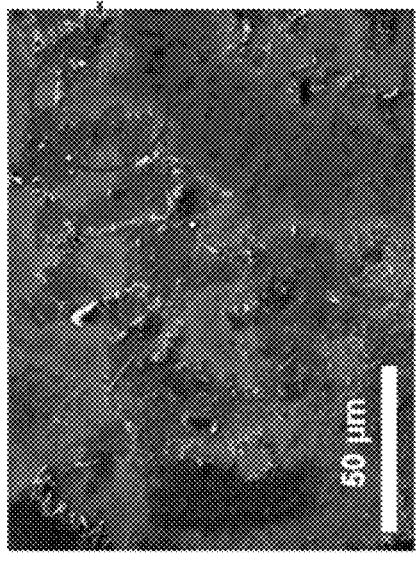
FIG. 16B
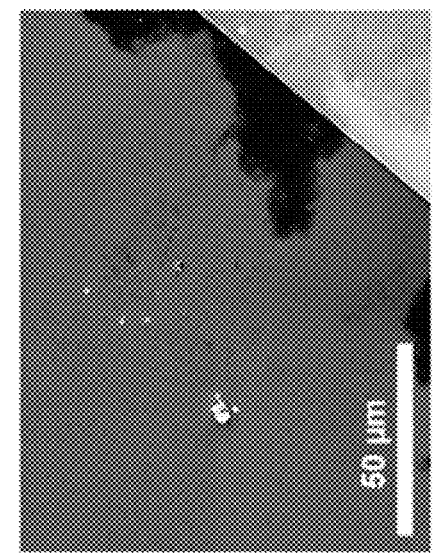
FIG. 16C Pure F-SWCNTs
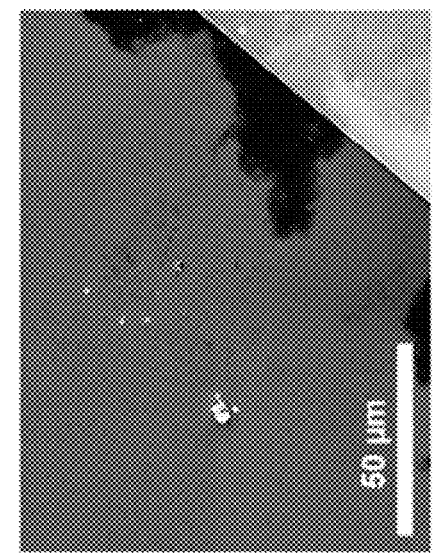
FIG. 16D Infused F-SWCNTs:Fe(tpp)ClO$_4$

|  | $H_2S$ | $O_2$ | $NO_2$ |
|---|---|---|---|
| $V_g > 0$ | high | med | low |
| $V_g = 0$ | med | high | med |
| $V_g < 0$ | low | med | high |

FIG. 27

SENSORS INCLUDING REDOX-ACTIVE SELECTOR COMPLEXES

CLAIM OF PRIORITY

The application claims priority to U.S. Provisional Application No. 62/560,186, filed Sep. 18, 2017, which is incorporated by reference in its entirety.

FEDERAL SPONSORSHIP

This invention was made with Government support under DMR1410718 awarded by the National Science Foundation. The Government has certain rights in the invention.

FIELD OF THE INVENTION

The invention relates to sensors including redox-active metal complexes.

BACKGROUND

Carbon monoxide is an analyte of considerable importance, particularly for safety reasons. Currently available methods for determining the concentration of carbon monoxide can suffer from high cost and impracticality of implementation in the field.

SUMMARY

In one aspect, a sensor can include a conductive region in electrical communication with at least three electrodes, the conductive region including a conductive material and a redox-active selector configured to bind an analyte more readily in a first redox state compared to a second redox state.

In another aspect, a method of sensing an analyte can include exposing a sensor to a sample, the sensor including a conductive region in electrical communication with at least three electrodes, the conductive region including a conductive material and a redox-active selector configured to bind an analyte in the sample more readily in a first redox state compared to a second redox state; and measuring an electrical property at the electrodes.

In another aspect, a method of preparing a sensor can include forming a conductive region in electrical communication with at least three electrodes, the conductive region including a conductive material and a redox-active metal complex configured to bind an analyte in the sample more readily in a first redox state compared to a second redox state.

In some circumstances, the redox-active selector can be a compound that selectively binds an analyte with different affinities for the analyte when in at least two distinct oxidative states. In some circumstances, the redox-active selector is a redox-active metal complex. In other circumstances, the redox-active selector is an organic compound. The organic compound can be a non-metal-containing compound.

In some circumstances, the conductive material can include a carbon material.

In some circumstances, the carbon material includes amorphous carbon, graphene, graphite, a single walled carbon nanotube, or a multiwalled carbon nanotube.

In some circumstances, the conductive material can be a conductive polymer.

In some circumstances, the analyte can be carbon monoxide.

In some circumstances, the analyte can be a sulfide, for example, $H_2S$.

In some circumstances, the redox-active selector can include a metal complex capable of forming a stable complex with carbon monoxide.

In some circumstances, the redox-active selector can include iron.

In some circumstances, the conductive material can include a ligand that binds the redox-active selector.

In some circumstances, the ligand can be a nitrogen-containing ligand bound to a carbon-based conductive material.

In some circumstances, the ligand that binds the redox-active selector can be covalently connected to the conductive material.

In some circumstances, the redox-active selector can be an iron porphyrin complex.

In some circumstances, the redox-active selector can be a triphenylmethyl compound.

In some circumstances, the three electrodes can include a source electrode, a drain electrode and a gate electrode.

In some circumstances, the method can include applying a negative gate voltage.

Other aspects, embodiments, and features will be apparent from the following description, the drawings, and the claims.

BRIEF DESCRIPTION OF THE DRAWINGS

FIGS. 7A-7D depict properties of a sensor.
FIGS. 11A-11C depict properties of a sensor.
FIGS. 16A-16D depict micrographs of a sensor material.
FIG. 27 depicts properties of a sensor.

DETAILED DESCRIPTION

Figure 1:
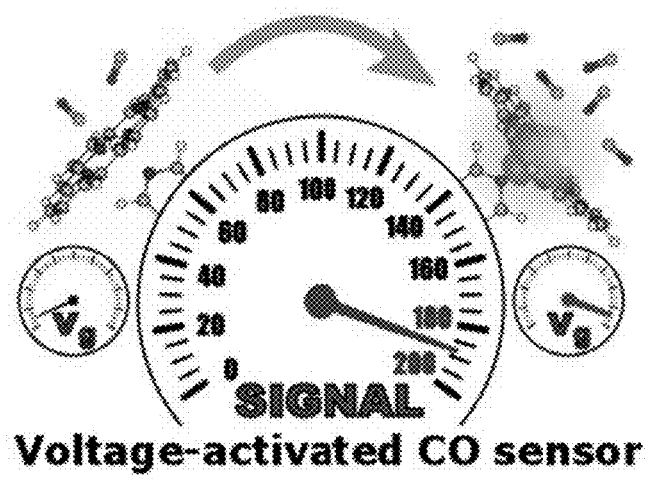
FIG. 1 depicts a sensor scheme.

A platform for voltage-activated, chemiresistive gas detection based on a conductive material, for example, covalently functionalized single-walled carbon nanotubes (SWCNTs), decorated with voltage-responsive chemical selectors has been developed. The sensor can be highly selective towards carbon monoxide over oxygen, nitrogen, and carbon dioxide and is robust to humidity and remains operational in air. FIG. 1 depicts the voltage response selectivity of the sensor. A construction is introduced that has a voltage activated receptor/selector attached electronically coupled to a conductive nanocarbon material. The nanocarbon can be amorphous carbon, graphene, graphite, single walled carbon nanotubes, multiwalled carbon nanotubes. By applying a voltage bias to the active elements of the device one can modulate the state of the sensor causing it to be more or less sensitive to a chemical signal of interest. The method requires that the selector/receptor is capable of having multiple redox states and optimal performance will be achieved with the interactions between the sensor and the target analyte are highly dependent upon the redox state of the selector.

Carbon monoxide (CO) outcompetes oxygen when binding to the iron center of hemeproteins, leading to a reduction in blood oxygen level and acute poisoning. Harvesting this strong and specific interaction between the CO and heme-inspired iron porphyrin provides promises for highly selective and customizable sensors that are viable alternatives to technologies based on mass spectroscopy and optical detection systems. Field-effect transistor (FET)-based sensors can detect CO with voltage-modulated sensitivity comprising iron porphyrin and functionalized carbon nanotubes (CNTs). FET-based devices offer an extra dimension of sensing through modulation of the gate voltage. Specifically, the sensors show significant increase in signal strength when negative gate voltage is applied. UV-Vis and differential pulse voltammetry reveal that the in situ reduction of $Fe^{3+}$ to $Fe^{2+}$ enhances the interaction between the decorated CNTs and CO. The sensors are selective to ppm levels of CO and are functional in air. The results provide a step toward the development of a novel platform of voltage-activated sensors based on highly specific chemical interactions.

Carbon nanotube-based chemical sensors are a promising alternative to established analytical methods for monitoring the concentration of toxic gases. These sensors are highly selective, inexpensive, functional under low power with real-time detection, and modifiable to target specific analytes. Herein, a platform for voltage-activated chemiresistive gas detection has been developed based on covalently functionalized single-walled carbon nanotubes (SWCNTs) decorated with voltage-responsive chemical selectors. The selectivity arises from the recognition of CO by an iron-metalloporphyrin anchored to the pyridyl-functionalized SWCNTs. The sensor is highly selective towards CO over oxygen, nitrogen, and carbon dioxide and that it is robust to humidity and operational in air. The affinity of the iron-metalloporphyrin-functionalized nanotube towards CO can be modulated through the applied gate voltage. UV-Vis spectroscopy and differential pulse voltammetry indicate that increased sensitivity of the sensor towards CO arises from an in situ reduction of $Fe^{III}$ to $Fe^{II}$. These findings demonstrate the potential of a voltage-activated recognition in SWCNT-based sensors.

Carbon monoxide (CO) is responsible for more than half of all fatal poisoning worldwide.[1] Exposure to the colorless, tasteless, and odorless gas is difficult to discern as the initial symptoms of poisoning (headache, dizziness, and confusion) are nonspecific. In the United States, the Occupational Safety and Health Administration (OSHA) has designated permissible exposure limits of 50 ppm over eight hours and 200 ppm over five minutes. Ref 2. The affinity of iron porphyrin towards CO is well-documented for the enzymes cytochrome P450, hemoglobin, and myoglobin. Refs. 3-7. This high affinity for CO over $O_2$ of hemoglobin and myoglobin is the underlying mechanism of carbon monoxide poisoning in mammals. Refs. 8-9. Although detectors for CO are available, there remains a need for massively distributed sensors that are small and inexpensive to prevent poisoning in domestic and industrial environments. Single walled carbon nanotube (SWCNT) chemiresistors and chemical field effect transistors (ChemFET) have been shown to provide suitable platforms for the detection of various gases. Refs. 10-15. Random networks of functionalized SWCNTs have produced sensors that are inexpensive to fabricate, operate at room temperature, and have ultra-low power requirements. Refs. 16-17. Theoretical and experimental reports have suggested that CO does not engage in charge transfer with pristine SWCNTs, indicating the a chemical reactive interface is necessary. Refs. 18-20. Conductivity-based CO detection has been reported for carboxylate-containing, deformed, or doped SWCNTs, as well as SWCNTs dispersed in polymers or decorated with metallic nanoparticles. Refs. 19-24. Alternatively, non-chemiresistive examples of SWCNT CO detectors rely on other mechanisms including changes in capacitance and resonant frequency. Refs. 25-26.

Although as summarized CO detectors based on SWCNTs have been reported, none make use of an in situ activated selector to produce additional selectivity and sensitivity. Previously, a chemiresistive sensor using an organocobalt complex to bind CO has been reported. Ref. 27. The cobalt selector demonstrated exceptional selectivity in air; however, the mechanism of detection required mobility of the complex which was provided by a fluid matrix and the lowest experimentally detected concentration was 800 ppm. Dong et al. has reported heme-modified chromium electrodes capable of CO detection in $N_2$, but device-to-device reproducibility, selectivity, and air stability were not reported. Ref 28. Even with these successful examples, the responsivity of the selectors cannot be controlled externally, which may limit the functionality of the sensors.

The resistivity or conductivity of the sensor can change when the sensor is exposed to an analyte and a voltage is applied. A conductive material conducts electricity. The conductive material can include a carbon material, a conductive polymer, or a metal oxide. The conductive material can include a metal, an organic material, a dielectric material, a semiconductor material, a polymeric material, a biological material, a nanowire, a semiconducting nanoparticle, a nanofiber, a carbon fiber, a carbon particle, carbon paste, or conducting ink, or combination thereof. The conductive material can include an organic electronic material, a conductive polymer, a doped conjugated polymer, or a conductive inorganic material.

A conductive polymer can include a poly(fluorene), a polyphenylene, a polypyrene, a polyazulene, a polynaphthalene, a poly(pyrrole) (PPY), a polycarbazole, a polyindole, a polyazepine, a polyaniline (PANI), a poly(thiophene) (PT), a poly(3,4-ethylenedioxythiophene) (PEDOT), a poly(p- phenylene sulfide) (PPS), a poly(acetylene) (PAC), a poly (p-phenylene vinylene) (PPV), or a copolymer thereof.

Figure 2A:
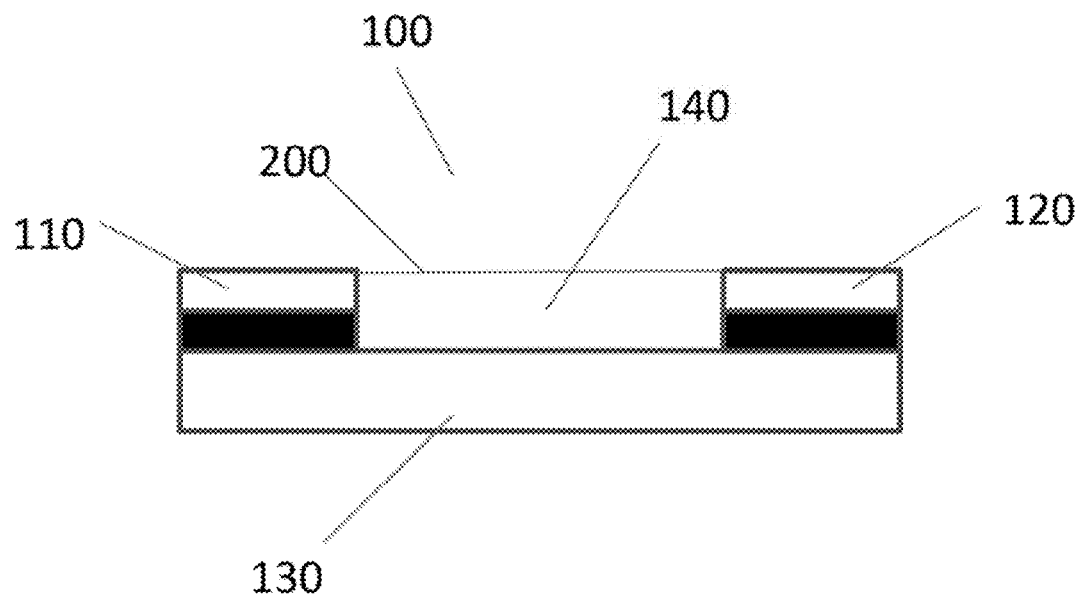
FIGS. 2A-2B depict a sensor.
Figure 2B:
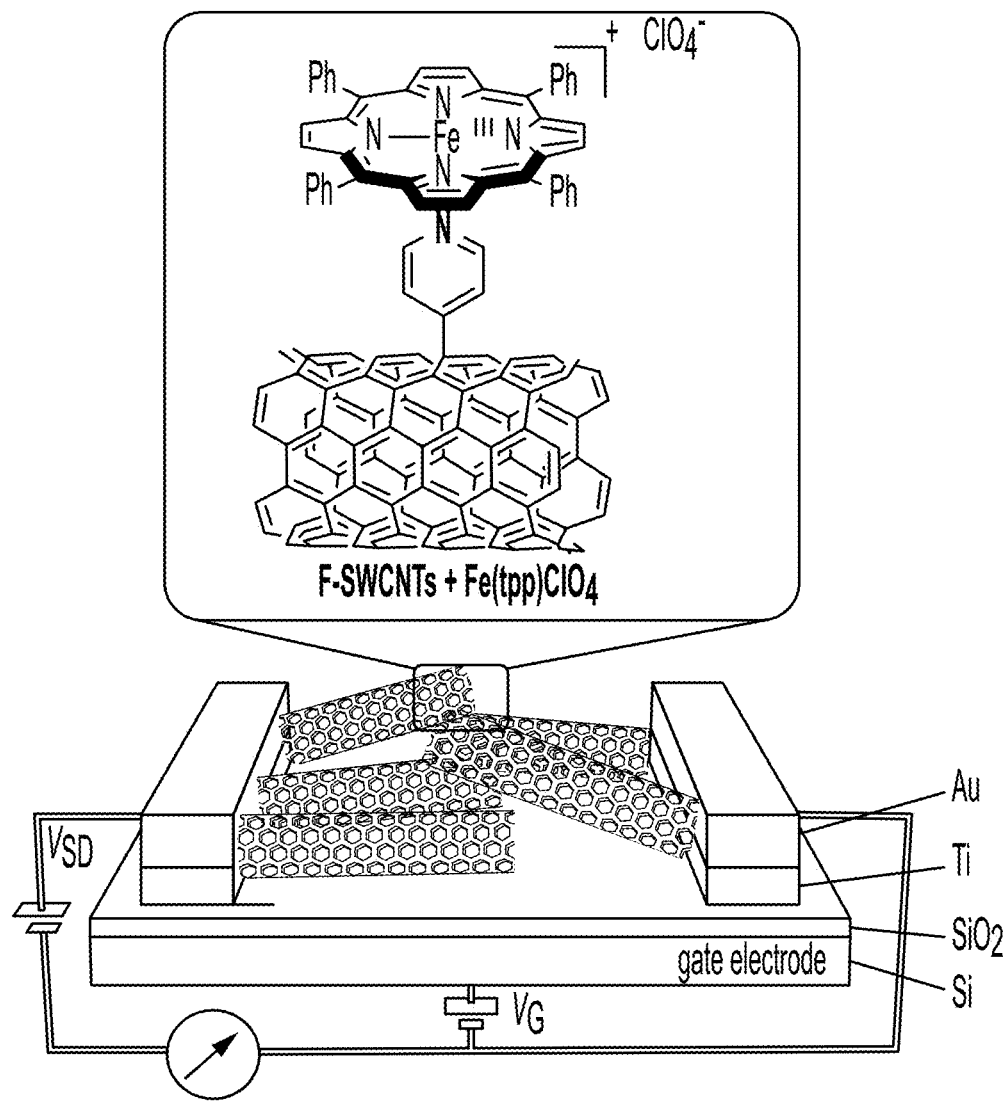

A selector with a predictive modulated responsiveness enables more information to be extracted from a single sensor element. To this effect, CO detectors are designed comprising pyridyl-functionalized SWCNTs as the matrix and bio-inspired iron porphyrin, a core element of many metalloenzymes/proteins, as a selector that can be activated and deactivated by modifying the gate voltage (FIGS. 2A-2B). Refs. 29-32. $Fe^{III}$ porphyrin is the persistent state in ambient atmosphere, however only the air sensitive $Fe^{II}$ binds CO. As a result, an applied gate voltage can transiently reduce the iron porphyrin in situ from $Fe^{III}$ to $Fe^{II}$ and thus enabling CO binding. The redox equilibration between SWCNTs and a $Fe^{II}$ porphyrin and the prospects for detecting CO have been analyzed computationally, for a system comprising two-SWCNTs covalently linked via an iron(II) porphyrin. Ref. 33. Additionally, iron porphyrin-based CO detection schemes have been investigated in biological systems. Ref. 34. A recently developed scheme for iodonium functionalization was applied to precisely attach single aromatic rings to the sidewalls of SWCNTs. Ref 35. This method allows us to confidently install a pyridyl group attached in the 4 position to the SWCNT for anchoring of the 5,10,15,20-tetraphenyl-porphyrin iron(III) perchlorate (Fe (tpp)$ClO_4$) that serves as a redox active CO binding site.

Referring to FIG. 2A, sensor 100 can include a first electrode 110, a second electrode 120, a third electrode 130 and a conductive material 140 in contact with each of the electrodes to create a conductive region 200. The electrodes can be insulated from each other as shown in black. The conductive material can be a conducting polymer, such as, for example, polyacetylene, polyaniline, polypyrrole, polythiophene, polyphenylene, polyphenylenevinylene, or other conducting complex or polymer. In other embodiments, the conductive material can be a carbon material, such as amorphous carbon, graphene, graphite, a single walled carbon nanotube, or a multiwalled carbon nanotube. The conductive material can be a combination of these materials.

The gap between electrodes can range from 0.1 mm to 10 mm. The layer thickness of the conductive material and the selector can be between 0.1 μm to 5 μm. The molar ratio between the selector and the conductive material can be between 5:1 and 100:1.

The conductive region can include a redox-active selector. The redox-active selector can be a transition metal complex that can change oxidation state, or redox state, by application of a voltage across two of the electrodes. The transition metal can be iron. The redox-active metal complex can be bonded to a ligand. The ligand can be covalently bonded to the conductive material. One redox state of the metal can bind an analyte more selectively than the other redox state of the same metal, leading to controllable sensitivity of the sensor. Alternatively, the selector can be a redox-active organic compound, for example, a triphenyl methane compound.

Figure 3:
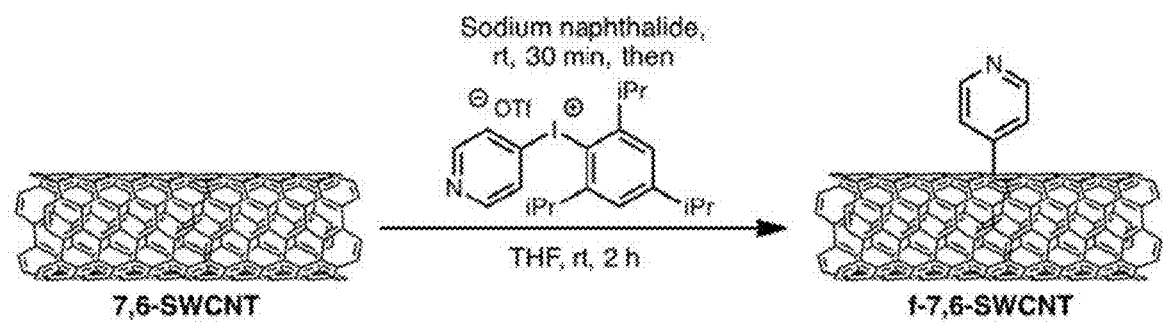
FIG. 3 depicts a ligand functionalized carbon material.
Figure 4:
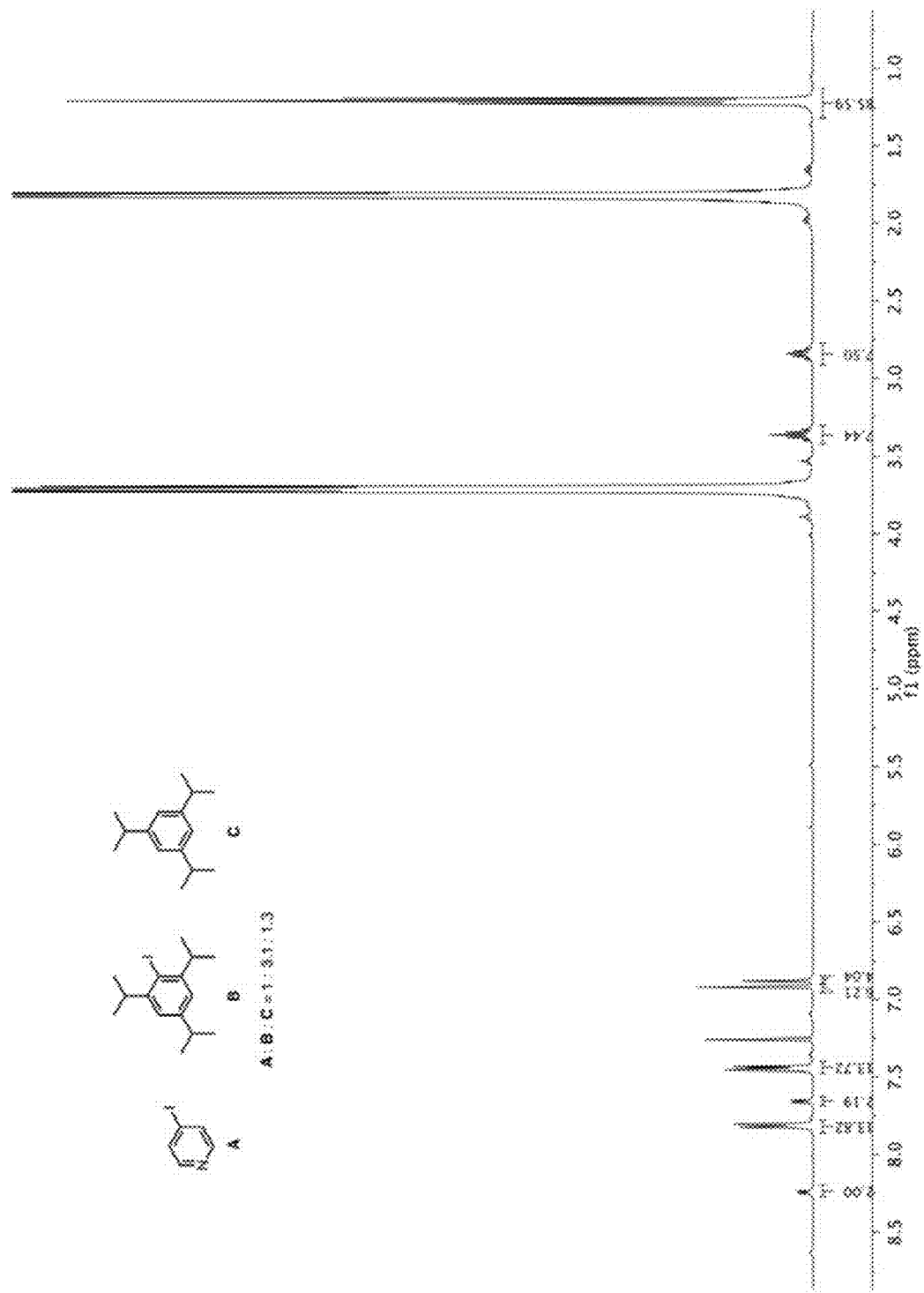
FIG. 4 depicts properties of a carbon material.
Figures 5A, 5B:
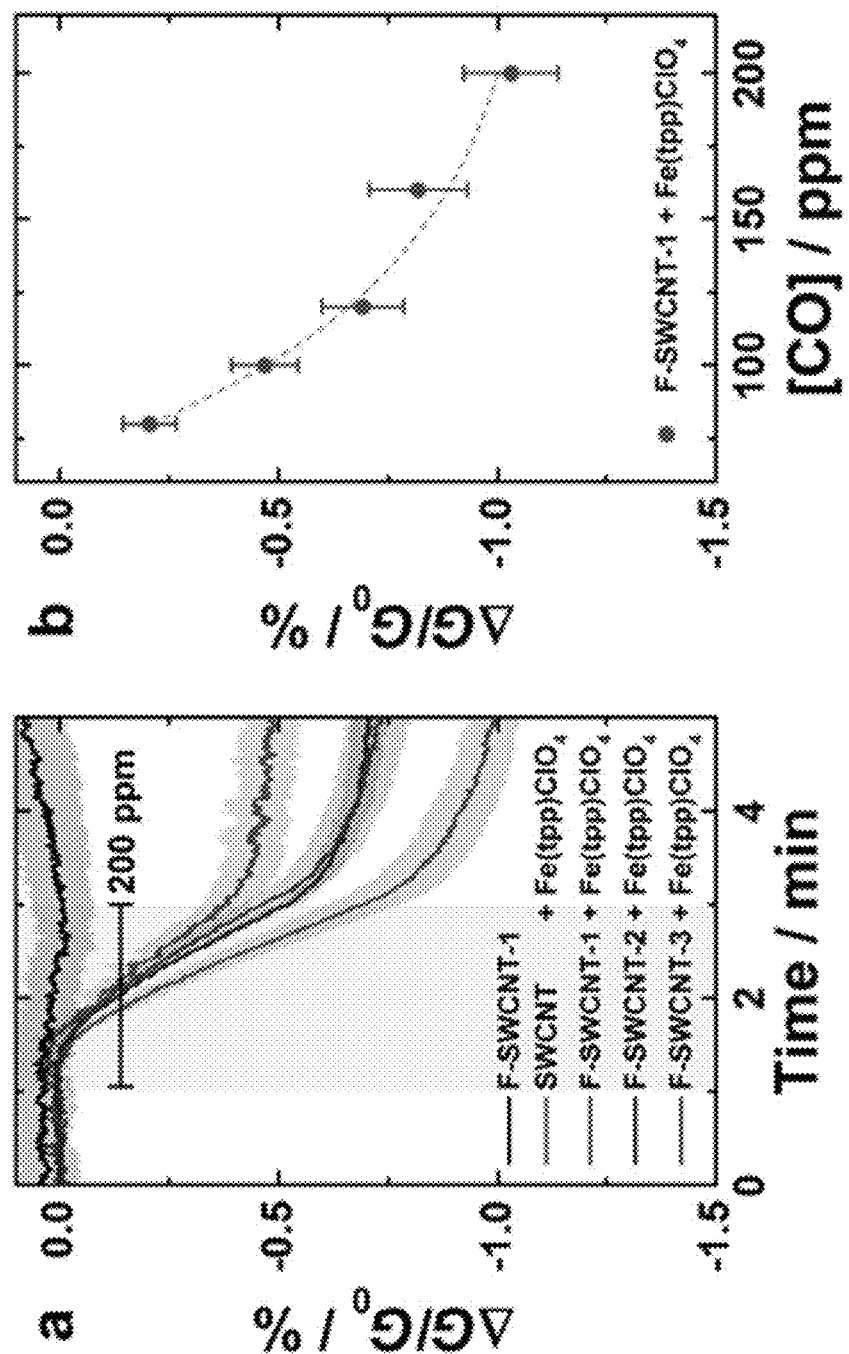
FIGS. 5A-5B depict properties of a sensor.

Referring to FIG. 2B, carbon monoxide detection can be accomplished by a bio-inspired sensors that harvest the CO-iron porphyrin interaction. FIG. 2B represents a schematic of a field-effect transistor (FET) substrate with Au source-drain electrodes, and Ti adhesion layer deposited on $SiO_2$ dielectric layer and Si gate electrode. Chemical structures of pyridyl-functionalized single wall carbon nanotubes (F-SWCNTs) and iron porphyrin (Fe(tpp)$ClO_4$), depicting the coordination chemistry of the pyridyl group to the iron center of the porphyrin. For the detection of CO in air, a scheme can be borrowed from biology. The heme group in hemoglobin bind CO very strongly which ultimately leads to carbon monoxide poisoning in mammals. In a detector a related functional group is used, as shown here. An iron porphyrin that is tethered to a carbon nanotube. Under ambient conditions, this iron porphyrin exists in its oxidized, ferric form iron III. In the body however, the reduced porphyrin is known to interact with $O_2$ and CO. Because of that, on a device, the iron porphyrin is reduced to its ferrous form (iron II) by applying a gate voltage. In developing an optimal sensor, the density of the CO binding and transducing sites is critical. The density of pyridyl groups can be controlled on the SWCNTs by the ratio of pristine SWCNTs to sodium naphthalide and pyridyl iodonium salt during synthesis, (FIG. 3). Using a ratio of 1:0.05:0.05 equivalents of pristine CNT, sodium naphthalide and iodonium salt, respectively, one obtained 1.4 pyridyl groups per 100 SWCNT carbon atoms (F-SWCNT-1). Ref 35. $^1$H NMR analysis of the post-functionalization filtrate confirmed that the pyridyl groups was the dominant functional group on the SWCNTs (FIG. 4). Doubling the amount of sodium naphthalide and iodonium salt in relation to the pristine SWCNTs increased the pyridyl concentration to 1.9 per every 100 SWCNT carbon atoms (F-SWCNT-2). Further doubling of the two reactants only resulted in a small increase of functionalization of 2.0 per 100 SWCNT carbon atoms (F-SWCNT-3). FIG. 5A shows the average change in conductance normalized to the initial conductance ($\Delta G/G_0$) of sensors with the different levels of functionalization in response to 2 min exposures of 200 ppm CO after a linear baseline correction. This post-acquisition data processing was used to mitigate the slight drift in the conductance of the sensors. Sensors without iron porphyrin-both pristine (not shown) and functionalized (black curve) SWCNTs-showed negligible responses to CO, which was consistent with the previous reports. Refs. 18-20 and 27.

FIGS. 5A-5B show sensing responses at no gate voltages. (a) Average changes in the conductance and standard deviations (N>6 sensors) in response to 2 min exposures to 200 ppm of CO for F-SWCNTs without Fe(tpp)$ClO_4$ (black), pristine SWCNTs with Fe(tpp)$ClO_4$ (green), and three densities of functionalization (red, blue, violet). (b) Conductance changes of F-SWCNT-1 with Fe(tpp)$ClO_4$ in response to various concentrations of CO gas diluted in $N_2$.

Sensors with iron porphyrin showed dosimetric responses indicating irreversibility over the experimental time frame. Pristine SWCNTs (lacking the 4-pyridyl anchor group) when treated with Fe(tpp)$ClO_4$ (green curve) showed a modest response (~0.57±0.09%). The response increased significantly with the introduction of sidewall pyridyl groups in F-SWCNT-1 (~1.08±0.05%). The increase of the signal reflects improved electronic communication and special organization of the SWCNTs and Fe(tpp)$ClO_4$. Differential pulse voltammetry (DPV) of pristine SWCNTs and F-SWCNT-1 treated with Fe(tpp)$ClO_4$ confirms that the pyridyl facilitates electron transfer to the Fe center (FIGS. 6A-6D). The decrease in conductance upon exposure to CO is consistent with the sensors comprising a p-type polymer and iron porphyrin reported by Paul et al.[36] Additionally, the observed decrease in conductivity of the sensors is consistent with the DFT prediction by Zhao and coworkers. Ref. 33.

Higher densities of pyridyl groups (F-SWCNT-2 and F-SWCNT-3) produced a decreased response (blue and purple curves), suggesting that a detrimental perturbation of the SWCNT $sp^2$ networks occurred with high levels of covalent functionalization. Refs. 37-39. As shown in the Ultraviolet-visible-near infrared (UV-Vis-NIR) spectra (FIG. 7D), the disappearance of the Van Hove transitions in F-SWCNT-2 and F-SWCNT-3 verified the degraded extended electronic structures of the SWCNTs. This result highlights the importance of balancing the degree of functionalization and preserving the native characteristics of the SWCNT.

Figure 8B:
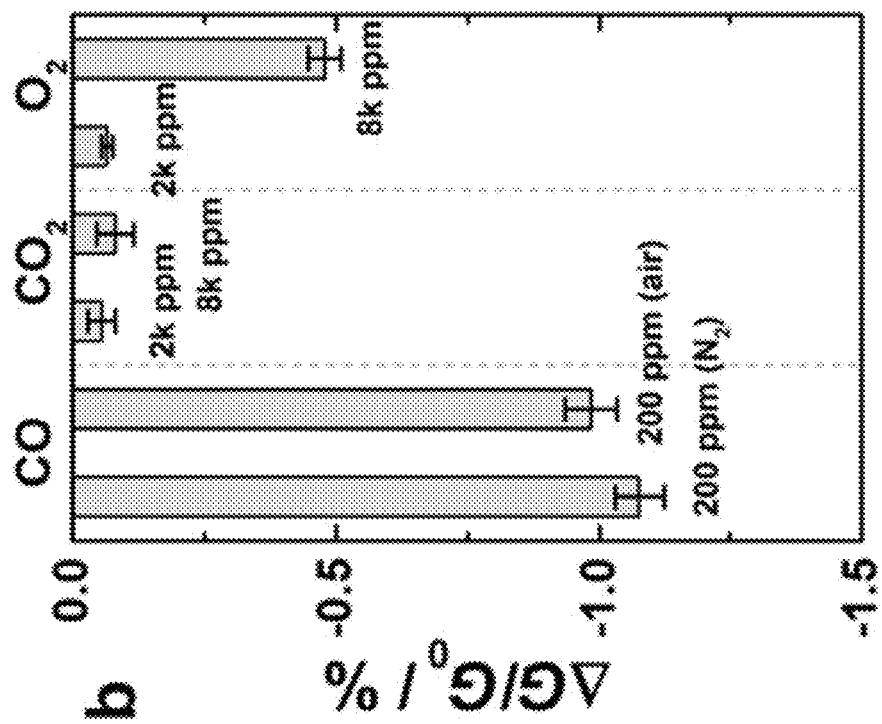
FIGS. 8A-8B depict properties of a sensor.
Figure 8A:
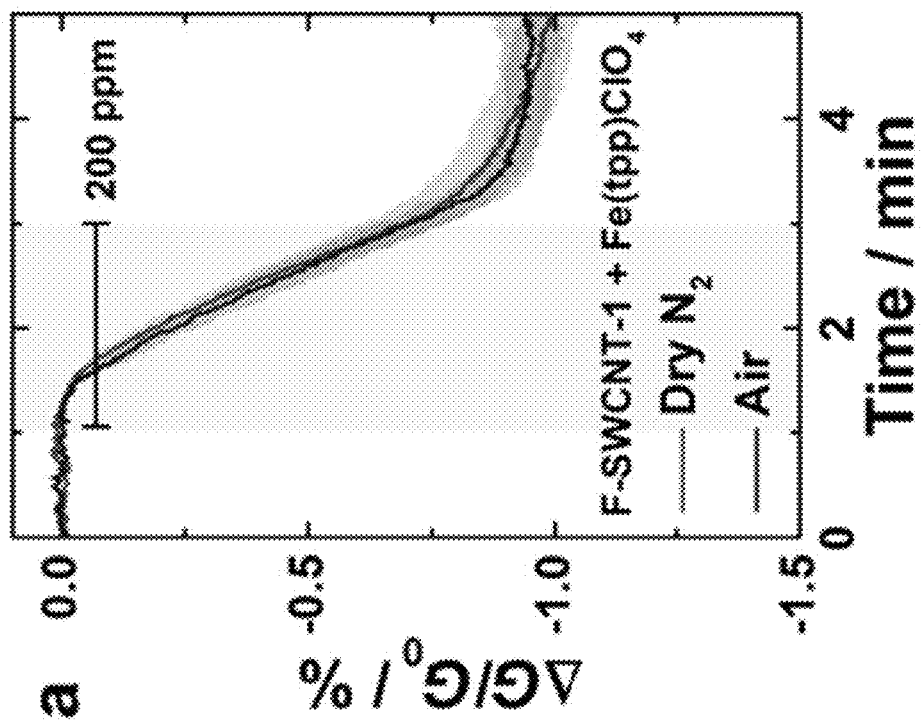

To evaluate the real-world applicability of the sensors, sensitivity and selectivity was investigated. FIG. 5B summarized the responses to various concentrations of CO. The lowest detected concentration was 80 ppm of CO in $N_2$, well within the range of industry standards for CO detectors (Table S3) and the OSHA's limit of 200 ppm during a 5 min period. Ref. 2. As a result of the irreversibility of the sensors, lower concentrations can be detected at longer exposure times. It was further determined that the CO sensors give robust responses in humid air (42% relative humidity) (FIG. 8A). FIG. 8B shows the responses to $CO_2$ and $O_2$. The sensors have negligible responses to 8000 ppm $CO_2$ (~0.08±0.04%). For $O_2$ at 8000 ppm (ambient atmosphere is 209,500 ppm $O_2$) a moderate response (~0.48±0.03%) was observed. These findings reflect the relative binding strengths between iron porphyrin and selected small molecules ($CO>O_2>CO_2$). Ref. 40-42. The fact that CO outcompetes the binding of $O_2$ allows the sensor to operate under ambient conditions.

FIGS. 8A-8B show robustness and selectivity of the CO sensors. (a) Conductance curves of F-SWCNT-1 with $Fe(tpp)ClO_4$ sensors in response to 2 min of 200 ppm of CO gas in air (42% relative humidity) and dry $N_2$. (b) Comparison between the response to CO in both $N_2$ and air to the responses to $CO_2$ and $O_2$.

Figure 9A:
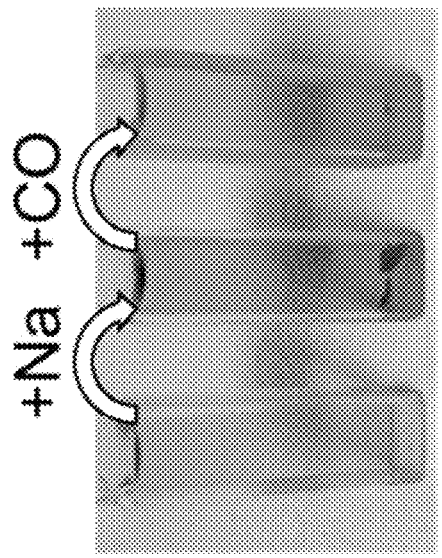
FIGS. 9A-9D depict properties of a sensor.
Figure 9B:
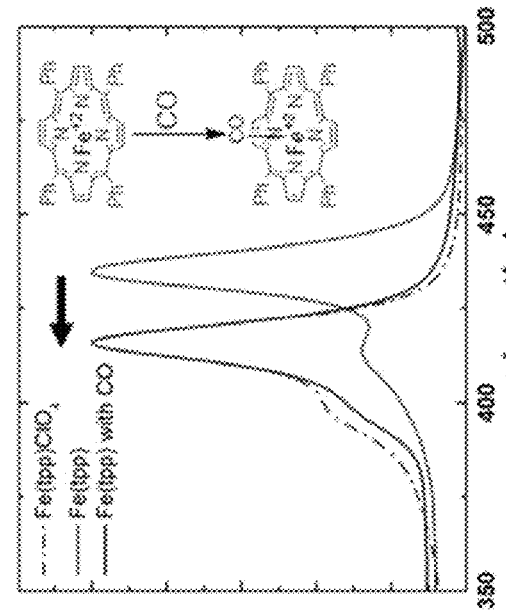
Figure 9C:
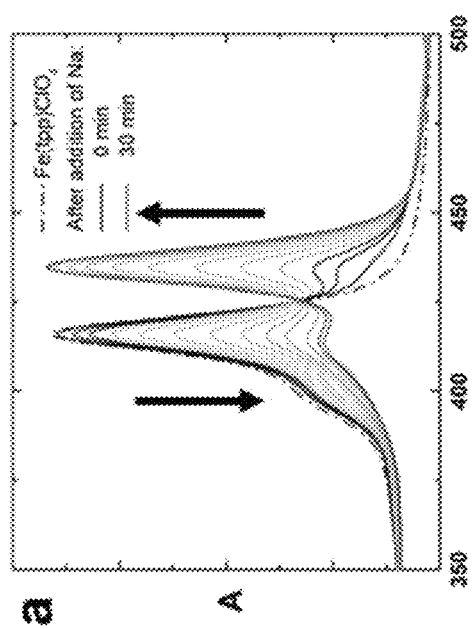
Figure 9D:
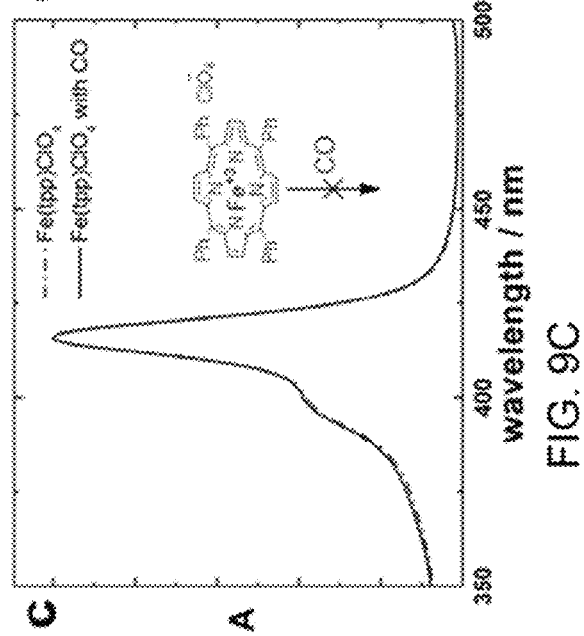
Figure 10A:
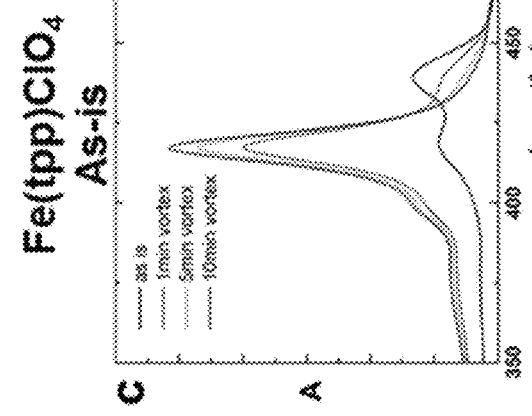
FIGS. 10A-10F depict properties of a sensor.
Figure 10B:
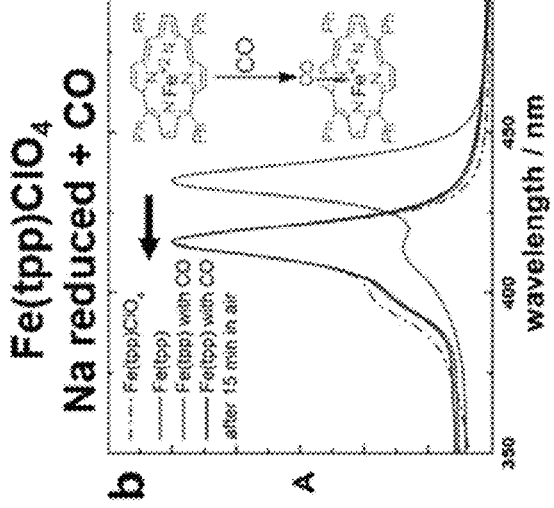

To verify that the sensing mechanism arises from the interaction between CO and iron(II) porphyrin, parallel solution studies were performed. Ref 43. $Fe^{III}(tpp)ClO_4$ can be chemically reduced to $Fe^{II}(tpp)$ in THF solution using Na metal; in the UV-Vis, this change is observed as a red shift of $\Delta\lambda=16$ nm (FIGS. 9A and 9B). The reduced species is moderately stable towards re-oxidation in air (FIG. 10A). Addition of CO to a THF solution of $Fe^{III}(tpp)ClO_4$ (FIG. 9C) produces no response, whereas $Fe^{II}(tpp)$ reacts quickly with CO as evidenced in a blue shift of $\Delta\lambda=16$ nm (FIGS. 9B, D). Ref. 34. It is noted here that this shift was stable after the removal of CO (FIG. 10B), which is consistent with the irreversible binding of CO to the porphyrin. The spectroscopic studies are in line with previous solution studies of CO binding to porphyrins. Ref. 44. Additionally, DPV of the composite of F-SWCNT-1 and iron porphyrin showed a decrease in intensity of the reduction peak from $Fe^{III}$ to $Fe^{II}$ when exposed to CO, (FIGS. 6A-6D). This observation is ascribed to the fact that CO attenuates the re-oxidation of $Fe^{II}$. Ref. 45. These findings support a hypothesis that in situ reduction of the iron porphyrin will provide for increased sensor response due to a stronger interaction with CO.

FIGS. 9A-9D show a UV-Vis investigation of reactivity of $Fe(tpp)ClO_4$ to CO in solution of THF. (a) $Fe(tpp)ClO_4$ before and at various times after addition of Na metal. (b) Photograph of the color change with the addition of sodium metal and subsequent addition of carbon monoxide. (c) Non-reduced $Fe(tpp)ClO_4$ before and after addition of CO. (d) Blue shift in the spectra of fully reduced porphyrin upon addition of CO. There is a strong response from reduced porphyrin upon exposure to CO. No response was measurable in the UV-Vis of the oxidized porphyrin upon exposure to CO. As expected, the UV Vis of the oxidized porphyrin in THF does not change upon exposure to 100% CO. The reduced porphyrin however shows a strong, immediate blue shift in the UV Vis upon exposure to CO. This shift is stable upon removal of CO from the headspace of the solution and mixing of the solution with air. Indicating that the binding of CO of the oxidized porphyrin is irreversible. This change can also be seen by the naked eye. The solution turns green upon addition of Na and then pinkish upon addition of CO.

Figure 10C:
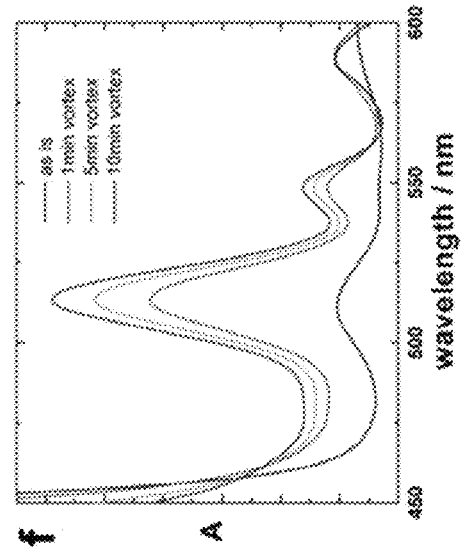
Figure 10D:
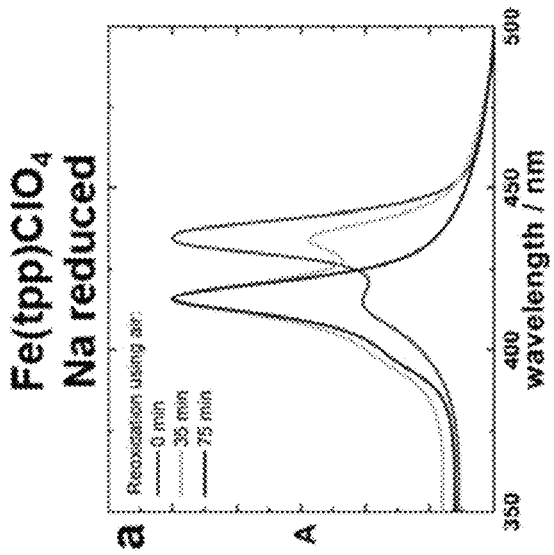
Figure 10E:
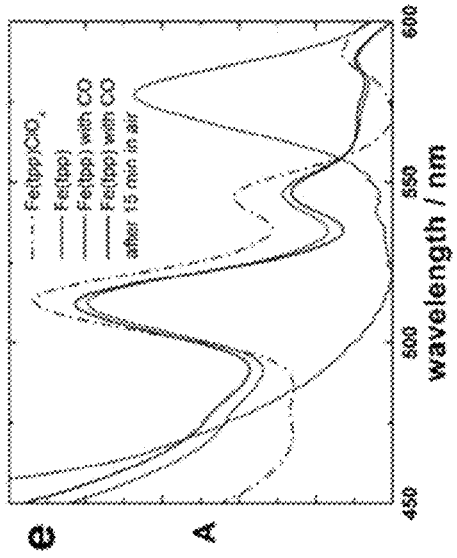
Figure 10F:
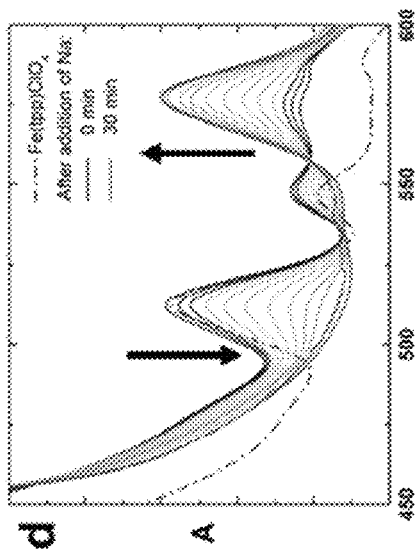
Figure 12:
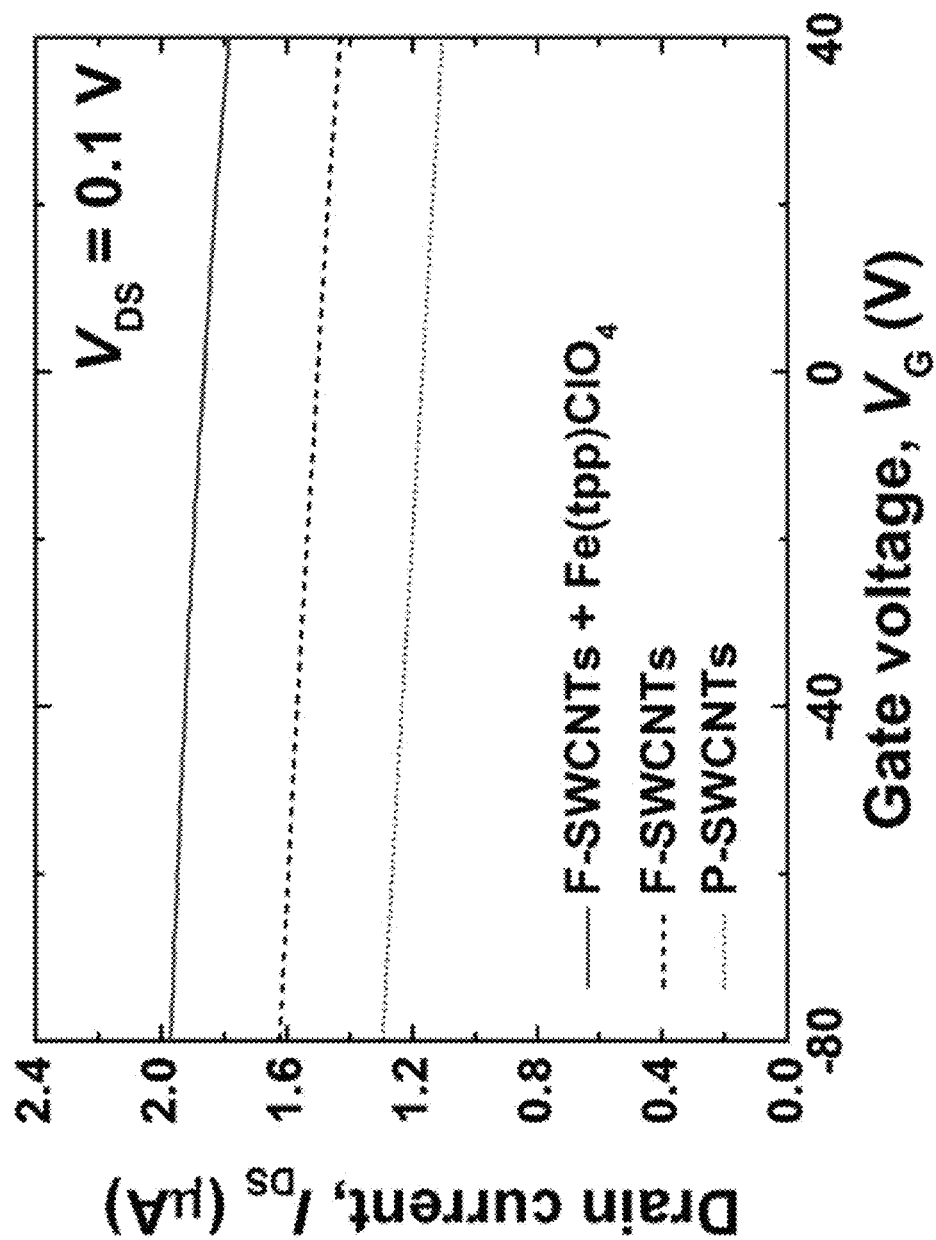
FIG. 12 depicts properties of a sensor.

Having established the base chemiresistive behavior, the effect of the applied gate voltage on the responsiveness of the sensors was investigated. Based on the UV-Vis and DPV investigations it was expected that the application of the gate voltage would affect the redox state of the iron porphyrin. FIG. 11A shows the average change in conductance of the sensors with the applied gate voltage of -3, 0, and 3 V when exposed to 200 ppm CO. FIG. 11B summarizes the change in conductance upon exposure to CO as a function of the applied gate voltage. At a gate voltage of -3 V, the response increased to -1.96±0.16%, nearly doubling the response at $V_G=0$. The response towards CO strongly increased upon application of negative gate voltage and decreased upon application of a positive gate voltage. It was determined that the semiconducting nature of F-SWCNT-1 is not responsible for this behavior as both the F-SWCNT-1 with and without $Fe^{III}(tpp)ClO_4$ (and P-SWCNTs) display metallic transfer characteristics (FIG. 12). UV-Vis spectroscopy reveals that the iron porphyrin was partially reduced by the SWCNTs when initially deposited on the sensors (FIG. 10C). This accounts for the enhanced sensitivity with $Fe^{III}(tpp)ClO_4$ addition and the attenuation of the response to CO under positive gate voltage. Inversely, the application of a negative gate voltage reduces the porphyrin in situ thereby increasing the affinity towards CO, the electron accepting ligand. The mechanism is attributed to a change in the Fermi energy level of the F-SWCNTs with applied gate voltage that then increases the proportion of reduced iron porphyrin. FIG. 11C schematically illustrates the in situ reduction of $Fe^{III}$ to $Fe^{II}$ with a change in the SWCNT Fermi level. Hence a stronger interaction between the $Fe^{II}$ center and the c-donating, it-accepting CO ligand can be achieved.

FIGS. 11A-11C show enhancement in sensitivity via application of the gate voltage. (a) Conductance curves of F-SWCNT-1 with $Fe(tpp)ClO_4$ sensors in response to 2 min of 200 ppm of CO at +3, 0, and -3 V gate voltage. (b) Change in conductance towards an exposure of 2 min at 200 ppm of CO as a function of the gate voltage. Dashed line to guide the eye. (c) Schematic of band diagram of SWCNT and $Fe^{III}py(tpp)ClO_4$ (py=pyridine) and interactions between the two upon application of gate voltage. Gate Voltage increases the $Fe^{II}py(tpp)ClO_4$.

After investigating the sensing mechanism and the purely chemisresistive behavior of the device, the influence of applied gate voltage to the sensor was investigated. This shows the average change in conductance of the sensors with the applied gate voltage of -3, 0, and 3 V when exposed to 200 ppm CO. FIG. 11B summarizes the change in conductance upon exposure to CO as a function of the applied gate voltage. At a gate voltage of -3 V, the response increased to -1.96±0.16%, nearly doubling the response at $V_G=0$. The mechanism is attributed to fully oxidizing/reducing the porphyrin in situ. In conclusion, a platform for the detection of CO with voltage-modulated sensitivity using the bio-inspired interaction between CO and iron porphyrin can be developed. The concept of using gate modulated redox states of receptors/selectors attached to SWCNTs is likely to have general applicability and similarly selective sensors for other analytes can be demonstrated.

Figure 13:
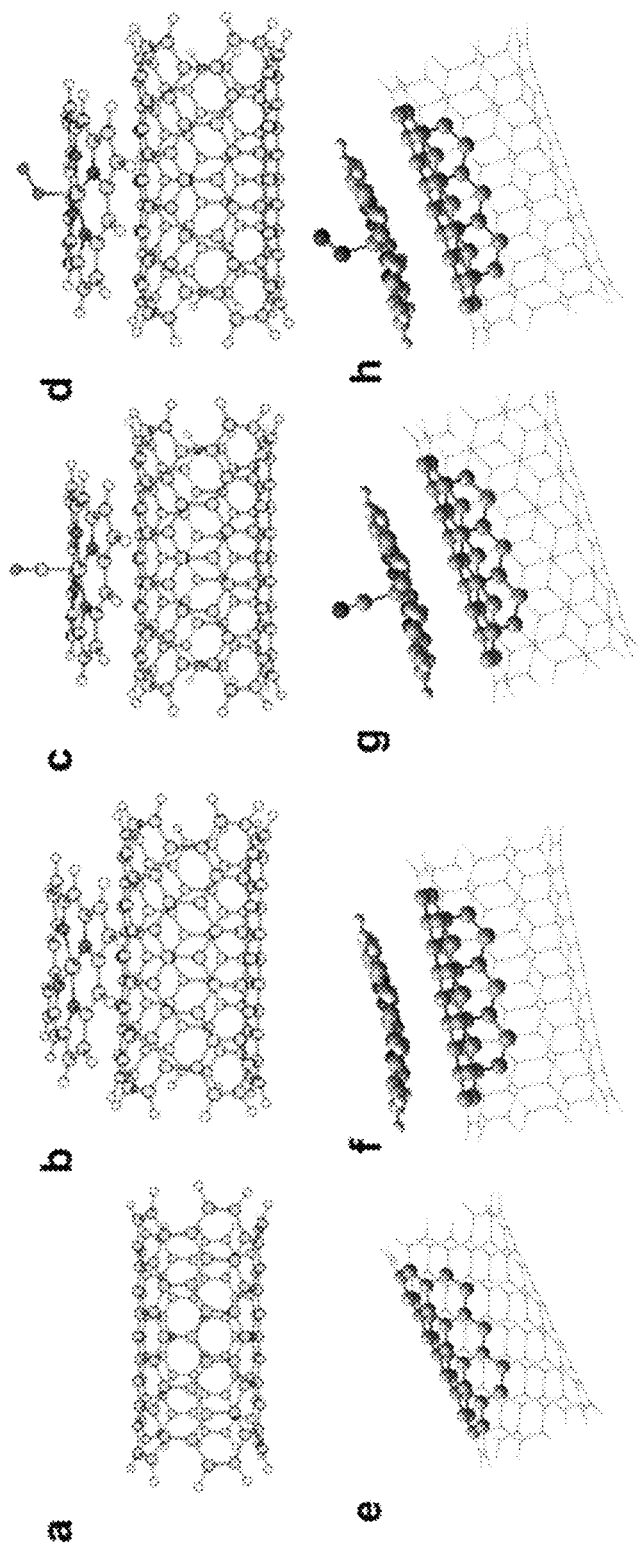
FIG. 13 depicts a carbon material.
Figure 14:
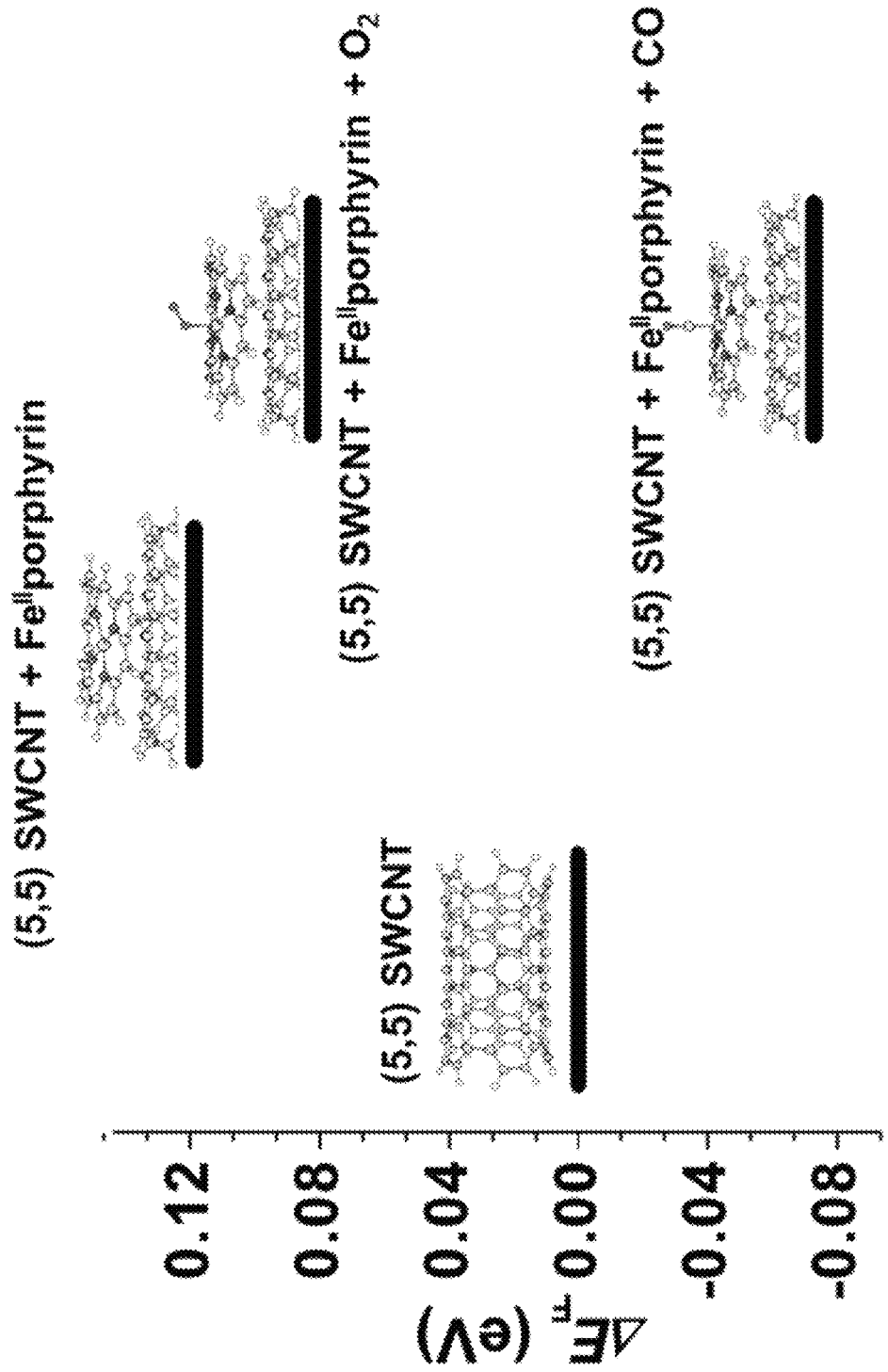
FIG. 14 depicts properties of a carbon material.
Figure 15A:
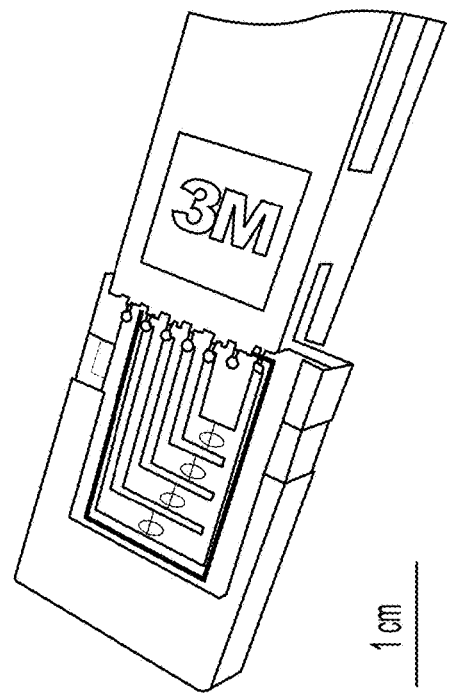
FIGS. 15A-15D depict a testing device.
Figure 15B:
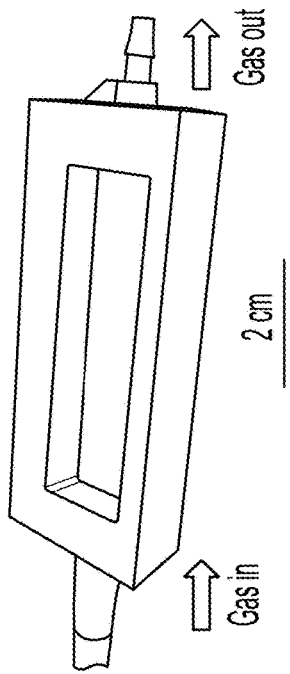
Figure 15C:
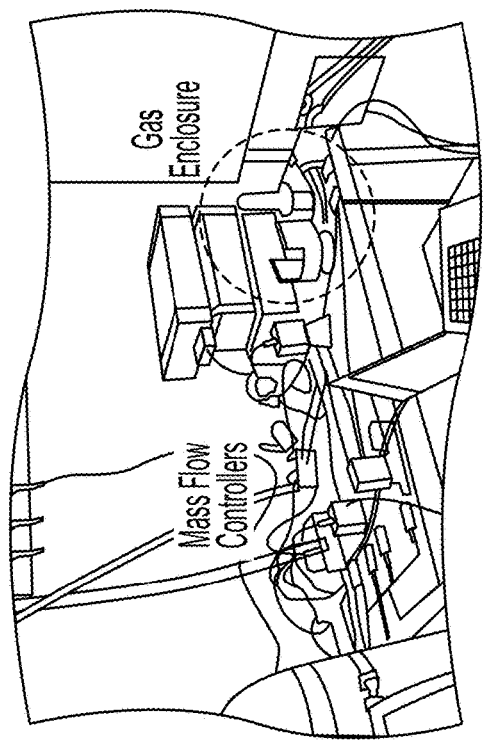
Figure 15D:
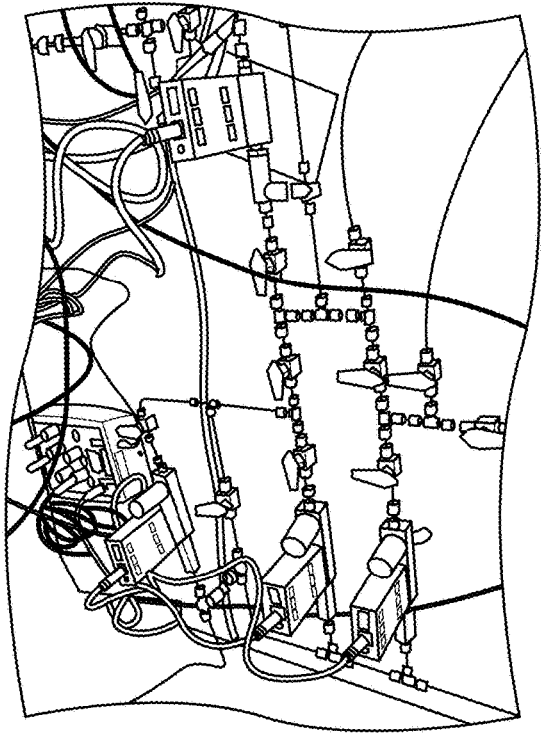

To gain further insights into the sensing mechanism, density functional theory (DFT) calculations were performed on a SWCNT fragment with $Fe^{II}$ porphyrin in the presence and absence of small gaseous ligands ($O_2$ and CO). A fragment of (5,5) SWCNT containing 110 carbon atoms end-capped with hydrogen atoms for comparison to established procedures was modeled. Refs. 46-48. This approach is similar to that used by Zanolli et al. who used the computed location of the Fermi level to illuminate the sensing behaviors of a gold-decorated SWCNT. Ref. 46. The ground-state geometries, computed distance between the SWCNT and Fe, the bond lengths between Fe and the ligands, binding angles between Fe and the ligands, and the charge transfer between SWCNT and porphyrin are shown in FIG. 13 and Table S4. FIG. 14 shows the change in computed Fermi energy ($\Delta E_f$) upon adsorption of $Fe^{II}$ porphyrin to a (5,5) SWCNT fragment and the subsequent binding of CO or $O_2$. The adsorption of $Fe^{II}$ porphyrin increased the Fermi level by 0.12 eV. Binding of CO and $O_2$ both reduced the Fermi level by 0.19 eV and 0.04 eV, respectively. Consistent with the sensing results, the binding of CO induced a more pronounced change when compared to the binding of $O_2$. This computed change in Fermi energy is in line with the trends of the sensing data and the decrease in conductance upon binding of CO and $O_2$. Although other sensing mechanisms have been reported, such as swelling of the SWCNT network or the junctions between electrode and SWCNT, electron transfer has been shown as the dominant factor in the majority of porphyrin-based SWCNT sensors. Refs 13, 44 and 49.

FIG. 14 shows a computed change in the Fermi energy ($\Delta E_F$) upon addition of $Fe^{II}$ porphyrin and subsequent addition of CO or $O_2$ relative to the Fermi energy of the pristine SWCNT with inserts of the ground-state geometries. For these molecules the Fermi level is defined as the level of the HOMO.

In conclusion, an amperometric platform for the detection of CO with voltage-modulated sensitivity using the bio-inspired interaction between CO and iron porphyrin can be developed. The importance of installing covalent pyridyl ligands on the SWCNTs for localizing and electronically coupling the iron porphyrins to the carbon nanotubes can be demonstrated. The application of the gate voltage can significantly enhanced the sensitivity of the sensors and show that this enhancement can be understood as resulting from an increase of $Fe^{II}$ porphyrin species can also be demonstrated. The sensors function in oxygenated and humid conditions and have sensitivities to meet the limits of detection required by OSHA. While the sensors can be competitive in terms of sensitivity and response time with commercial sensors, optimizations are not described herein. The concept of using gate modulated redox states of receptors/selectors attached to SWCNTs is likely to have general applicability and similarly selective sensors for other analytes can be demonstrated.

Figure 21:
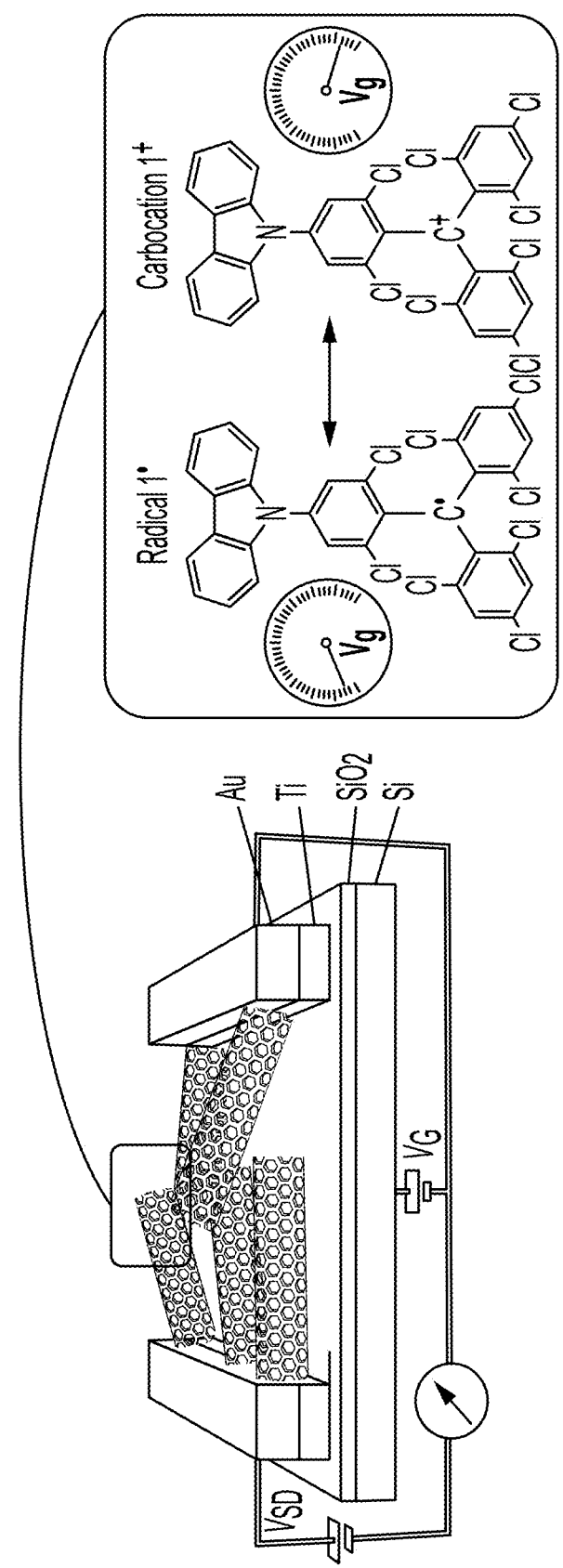
FIG. 21 depicts another embodiment of a sensor.
Figure 22:
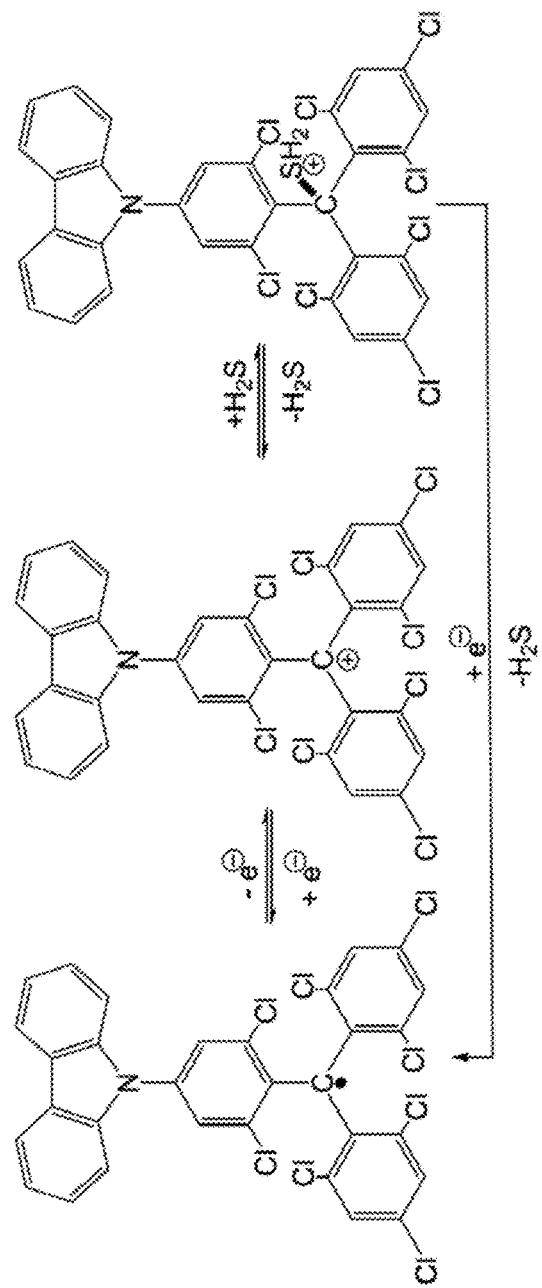
FIG. 22 depicts a redox selector.
Figure 23:
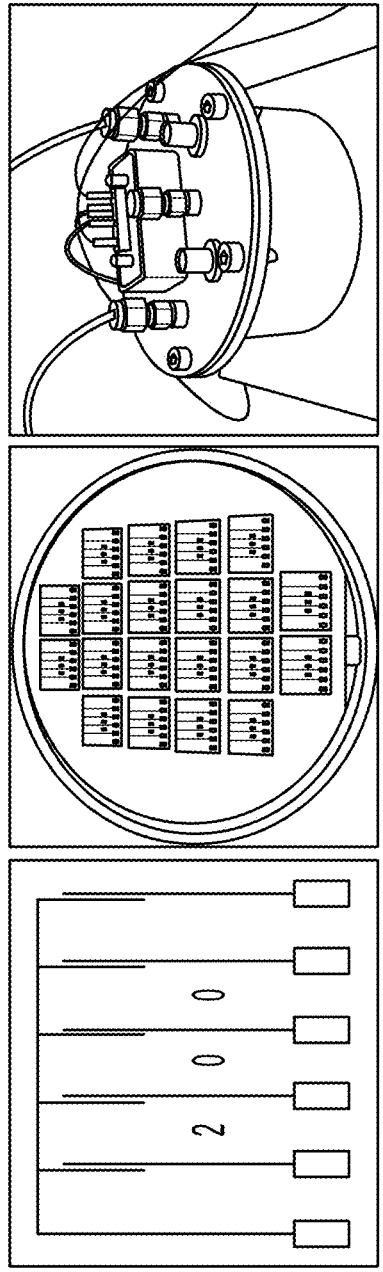
FIG. 23 depicts another embodiment of a sensor.
Figure 24:
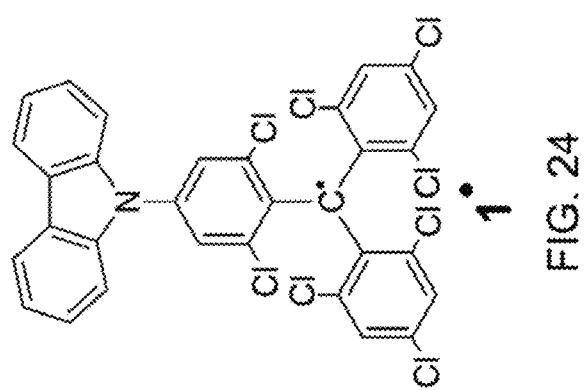
FIG. 24 depicts a redox selector.
Figure 25:
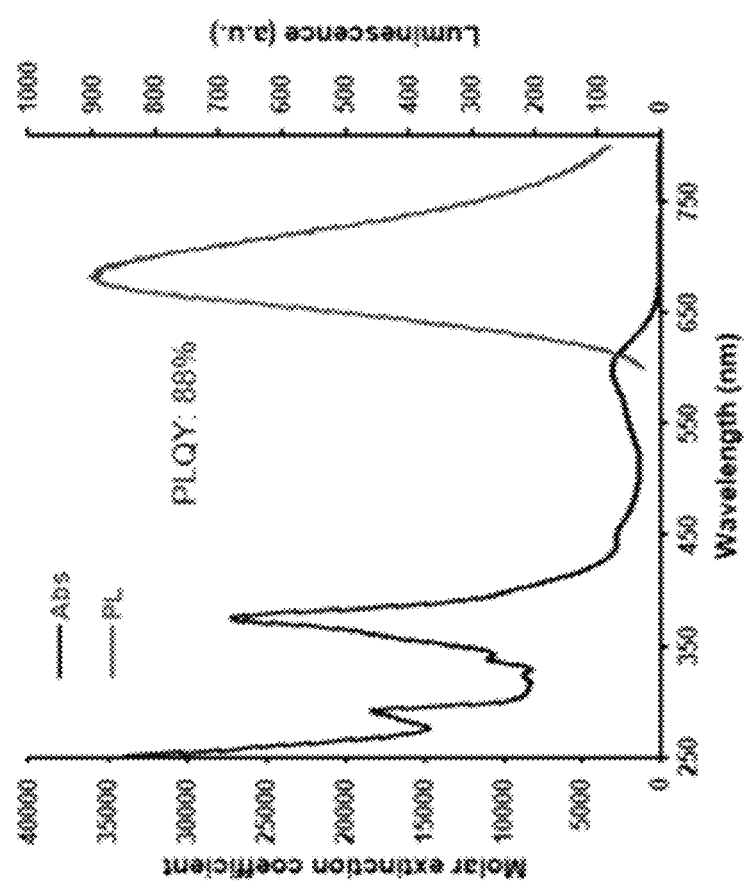
FIG. 25 depicts properties of a redox selector.
Figure 26:
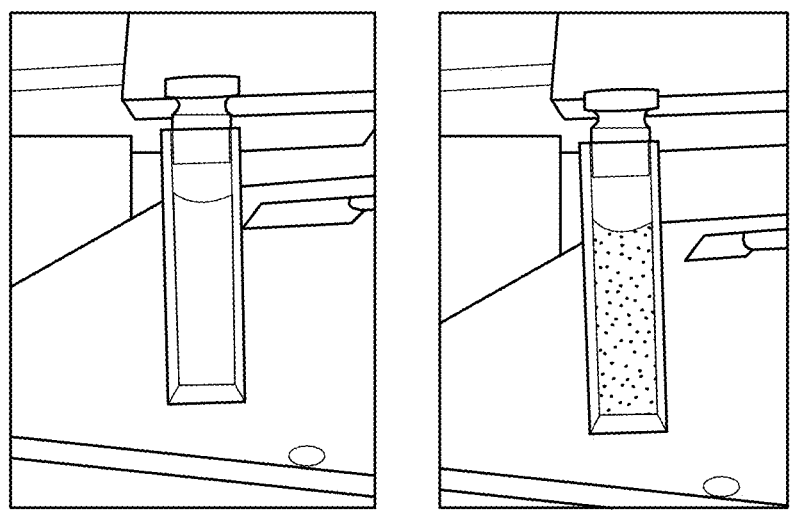
FIG. 26 depicts properties of a redox selector.
Figure 28:
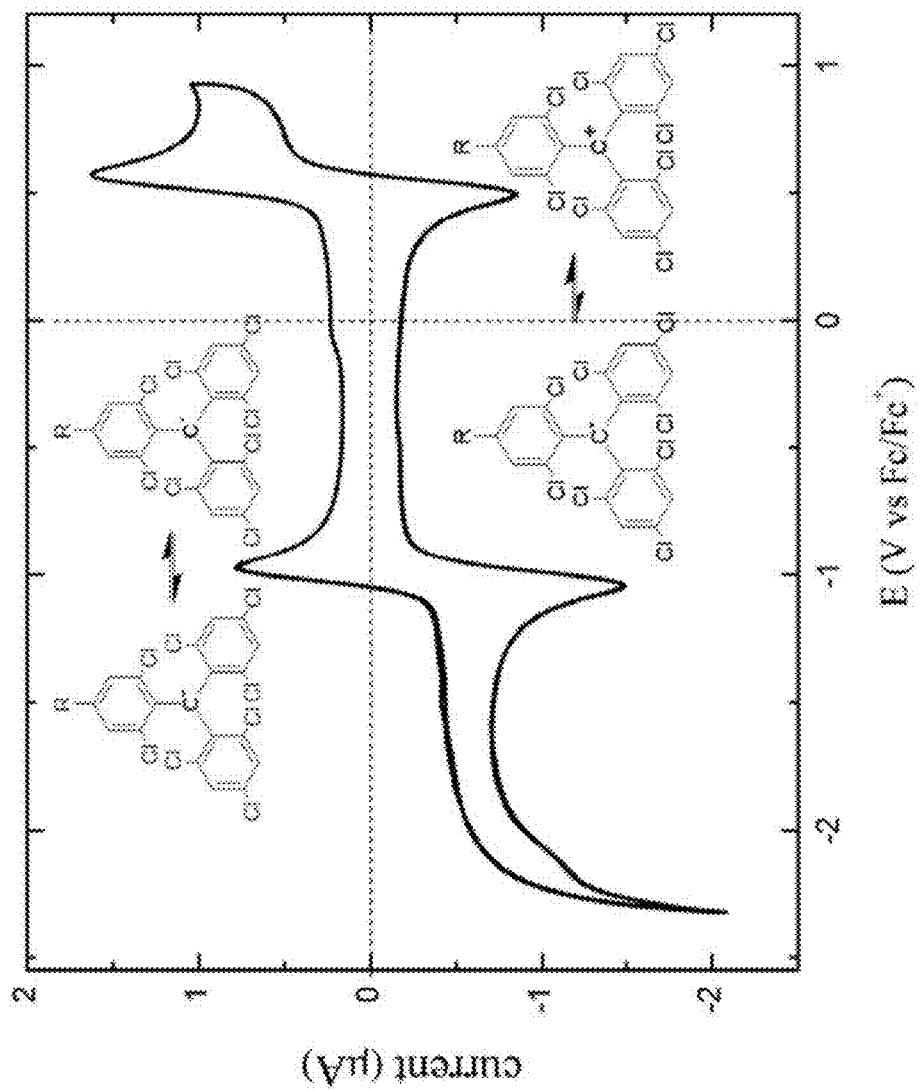
FIG. 28 depicts properties of a redox selector.

For example, as shown in FIGS. 21-36, the selector can detect other analytes. The sensor can be a gate voltage-controlled $H_2S$ sensor including a stable carbon-based radical selector 1. The FET-architecture allows in situ switching of redox state of 1 using gate voltage. Selectivity towards different analytes in on and off state of the sensor. The voltage-activated sensing scheme to can include include organic selector moieties, which can sense different analytes depending on the gate-voltage. A single-walled carbon nanotube (SWCNT) chemiresistor containing a stable organic radical 1 (a triphenyl methane compound) which can be reduced and oxidized reversibly, FIGS. 21 and 22. In its carbocationic form, the selector can interact favorably with $H_2S$ or $H_2S$ mimics (for example, 2,4-dithiapentane). In its carbanionic form, the selector can interact favorably with acidic analytes. FIG. 22 is a chemical scheme showing how a redox-active selector 1 can give rise to a reversible $H_2S$ sensor. A device testing scheme is shown in FIG. 23. The structure of the radical of 1 and its absorbance and fluorescence characteristics are shown in FIGS. 24, 25 and 26. Referring to FIG. 27, the sensitivity of the sensor or sensing device can be modified by adjusting the gate voltage. Target nucleophilic, radical, and electrophilic analytes can be detected with positive, neutral, and negative gate voltages.

Initially, the redox behavior of selector 1 was investigated in solution using cyclic voltammetry. See FIG. 28, which shows redox behavior of 1 in dichloromethane solution at a scan rate of 10 mV/s using tetra-n-butylammonium fluoride (TBAF) as the electrolyte, a glassy carbon working electrode, a Pt counter electrode, and a Ag/AgCl 1M reference electrode. In a solution of dichloromethane (DCM), the two-step oxidation and reduction of 1 is fully reversible at scan rates under 15 mV/s indicating that 1 is a suitable candidate for gate-voltage controlled sensing.

Figure 29:
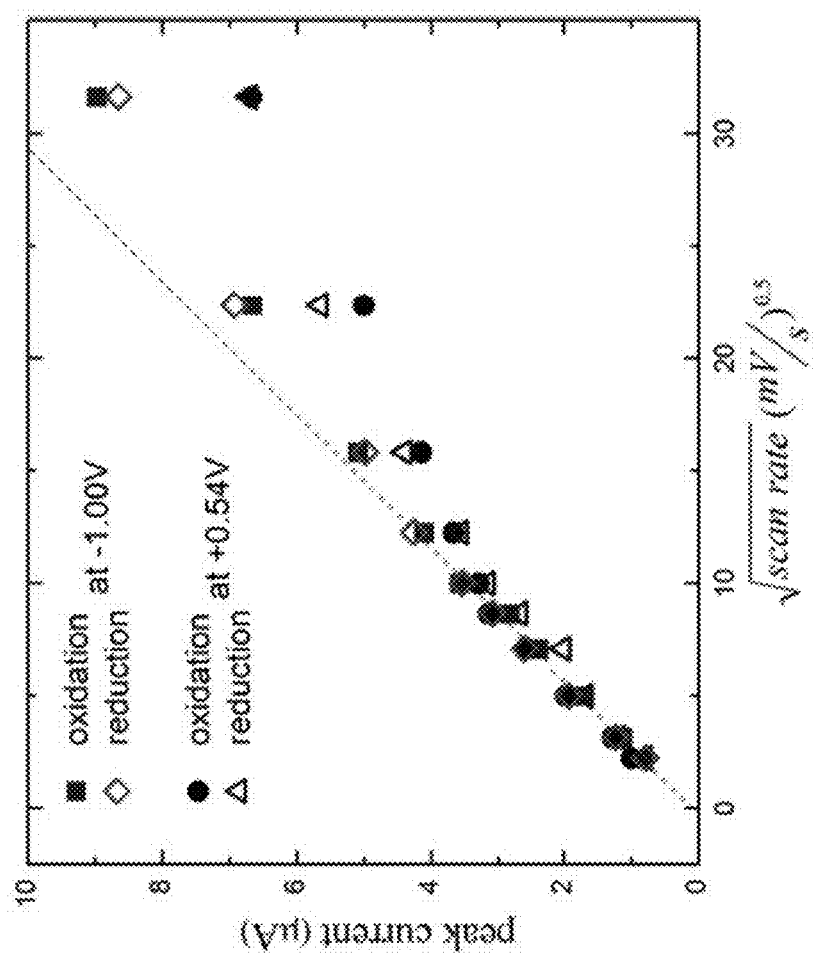
FIG. 29 depicts properties of a redox selector.
Figure 30:
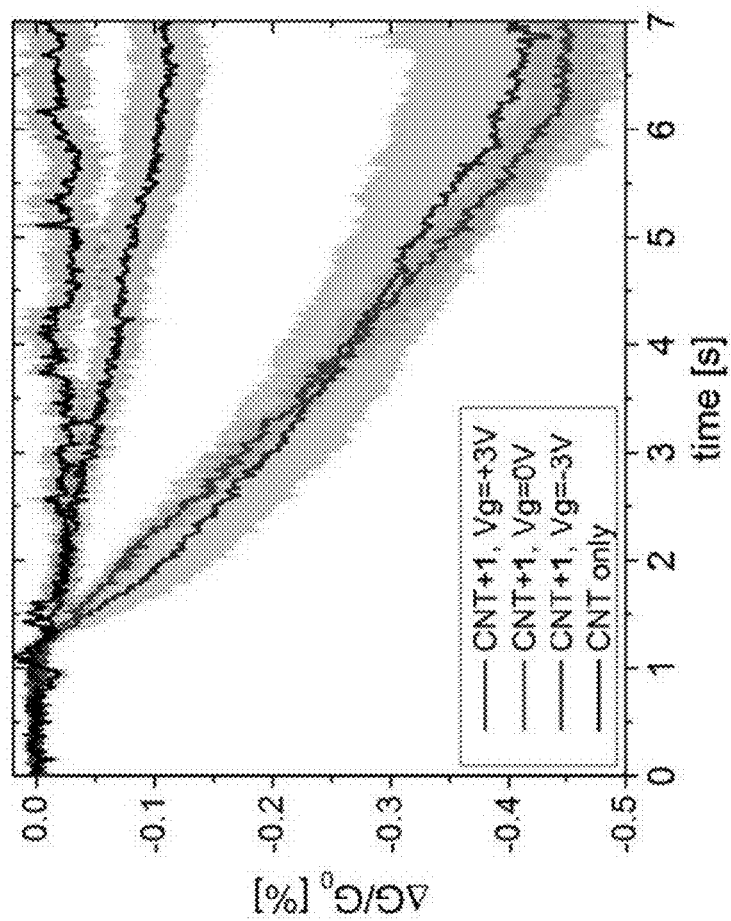
FIG. 30 depicts properties of a sensor.
Figure 31:
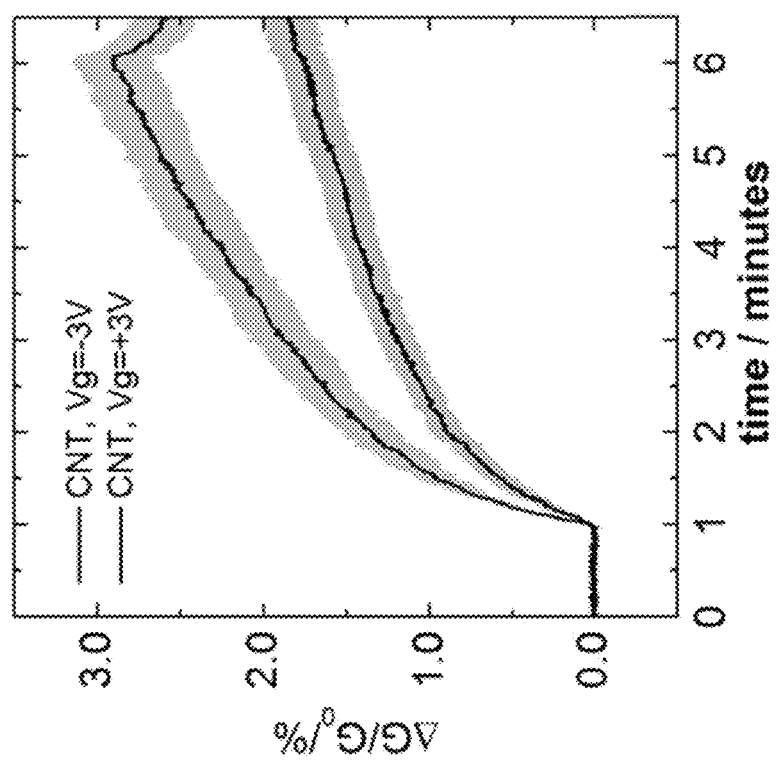
FIG. 31 depicts properties of a sensor.

Referring to FIG. 29, peak current of redox events of 1 is plotted against the scan rate to determine reversibility of redox events.

Preliminary sensing data was collected on the device performance under exposure to a $H_2S$ mimic (2,4-dithiapentane) and formic acid. See, FIG. 30. Sensing behavior of 1 towards $H_2S$ mimic (2,4-dithiapentane) and formic acid. (a) Sensing trace of device containing SWCNTs+1 towards 20 ppm 2,4-dithiapentane; CNT only control (black curve), negative gate voltage (blue curve), no gate-voltage (red curve), and positive gate voltage (purple curve). The sensors were connected to source-meter units (Keithley 4200) with a constant applied voltage across the source and drain ($V_{DS}$) and a variable gate voltage ($V_G$). Devices containing only SWCNTs show no response towards 2,4-dithiapentane. Similarly under negative gate-voltage, a SWCNT+1 device shows only a very small response towards 2,4-dithiapentane. Under zero or positive gate-voltage, a SWCNT+1 device demonstrated a fourfold increase in sensitivity towards 2,4-dithiapentane. Complementary, the sensitivity towards an acidic analyte, formic acid, can be increased 2.5-fold when applying a negative gate-voltage compared to a positive gate-voltage. These preliminary results demonstrate that the sensitivity of the organic selector 1 can be modulated using the gate-voltage. The selectivity of 1 as a function of the gate-voltage is also in line with our hypothesis that the carbocationic form interacts favorably with the $H_2S$ mimic (2,4-dithiapentane) and the carbanionic form of 1 interacts with acidic analytes.

Figure 32:
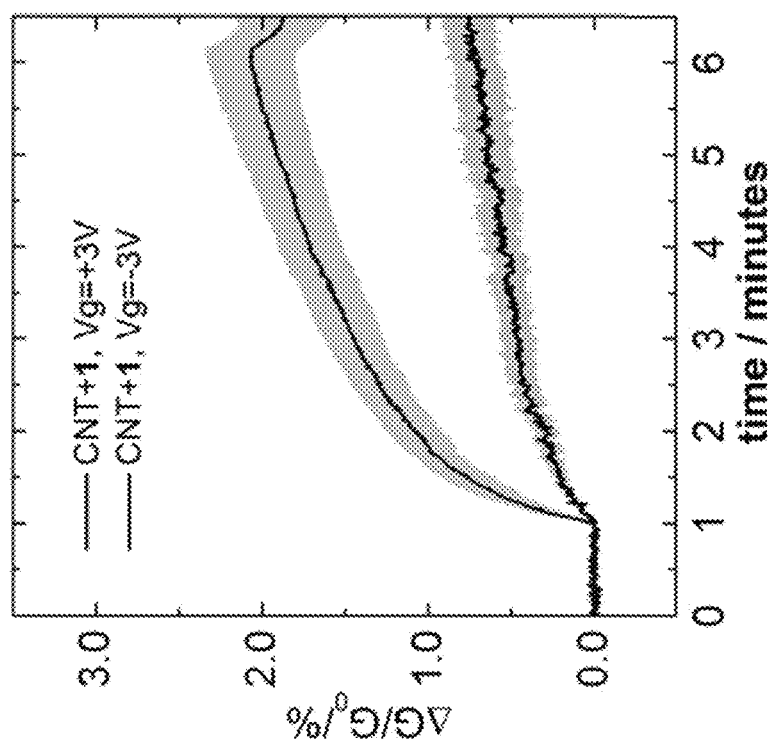
FIG. 32 depicts properties of a sensor.
Figure 33:
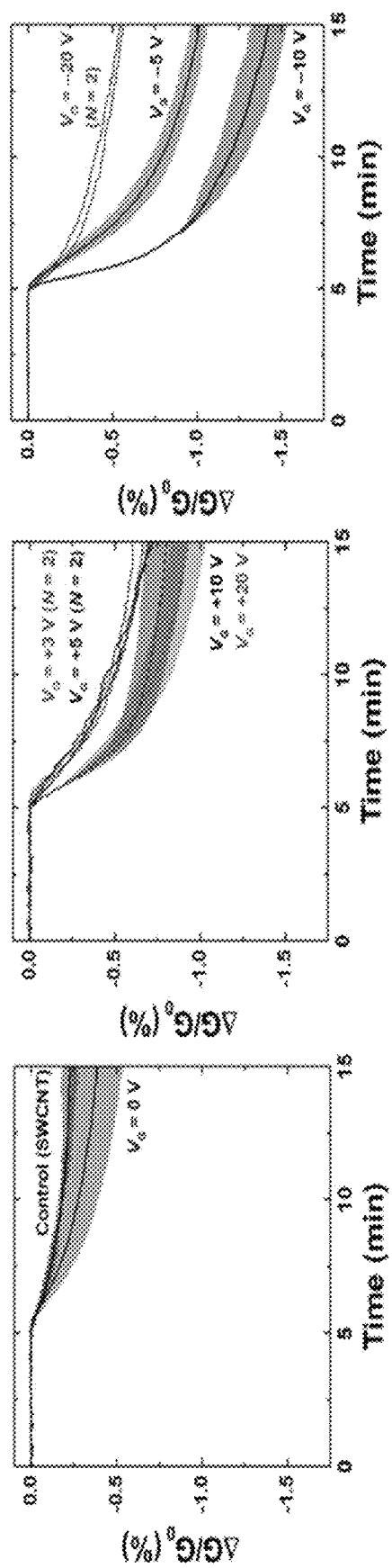
FIG. 33 depicts properties of a sensor.
Figure 34:
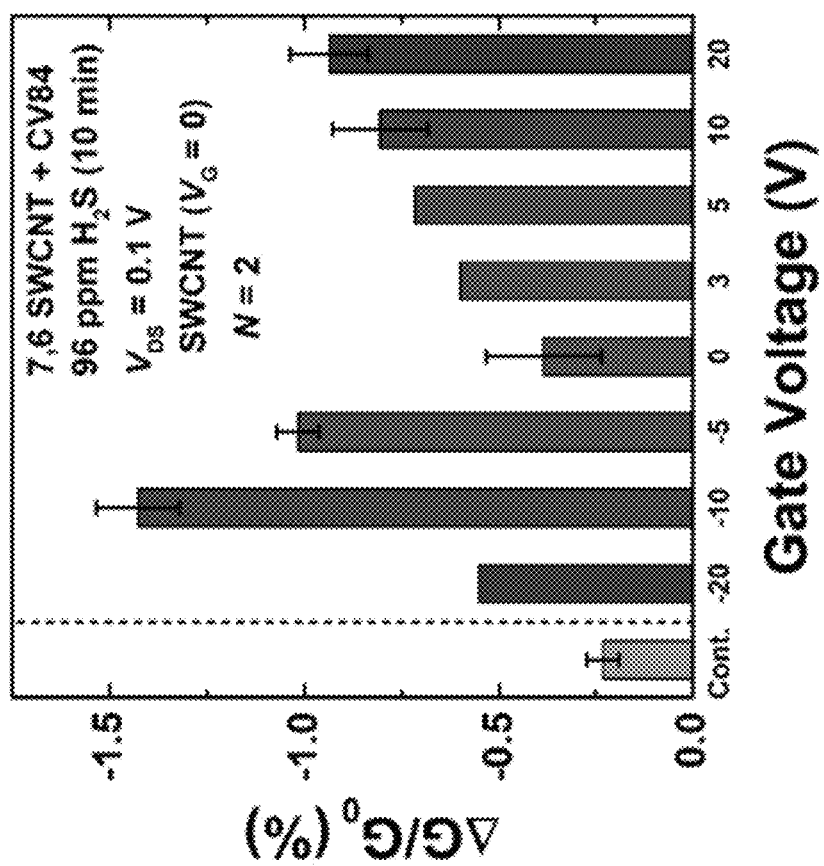
FIG. 34 depicts properties of a sensor.

Referring to FIG. 32, sensing trace of device containing SWCNTs+1 towards 300 ppm of formic acid is shown at positive (black curve) and negative (blue curve) gate-voltage.

The performance of a SWCNT+1 device was investigated in the sensing of $H_2S$. The preliminary data showed that selector 1 enhanced sensitivity towards $H_2S$. Initial experiments demonstrated that even at no applied gate voltage ($V_G$=0V) sensors comprising the selector and SWCNTs outperformed control devices with only SWCNTs. See FIGS. 34 and 35. Interestingly, the application of gate voltage in both positive and negative directions improve the sensitivity towards $H_2S$. The interaction of the current selector to $H_2S$ at the current stage appears to be irreversible. Thus, more optimization is required to obtain reversibility through the application of gate voltage.

The SWCNTs used for this work were purified SWCNTs with (7,6) chirality with >90% carbon content and >77% carbon as SWCNTs (0.7-1.1 nm diameter) purchased from Aldrich. Sensors were prepared on field-effect transistor-based substrates with a bottom gate, bottom contact configuration. Pristine SWCNTs were suspended in ortho-dichlorobenzene at a concentration of 0.25 mg mL$^{-1}$ and drop-casted onto the patterned substrates between the source/drain channels using a micropipette and the solvent was removed in vacuo. Each substrate contained four identical channels.

Figure 35:
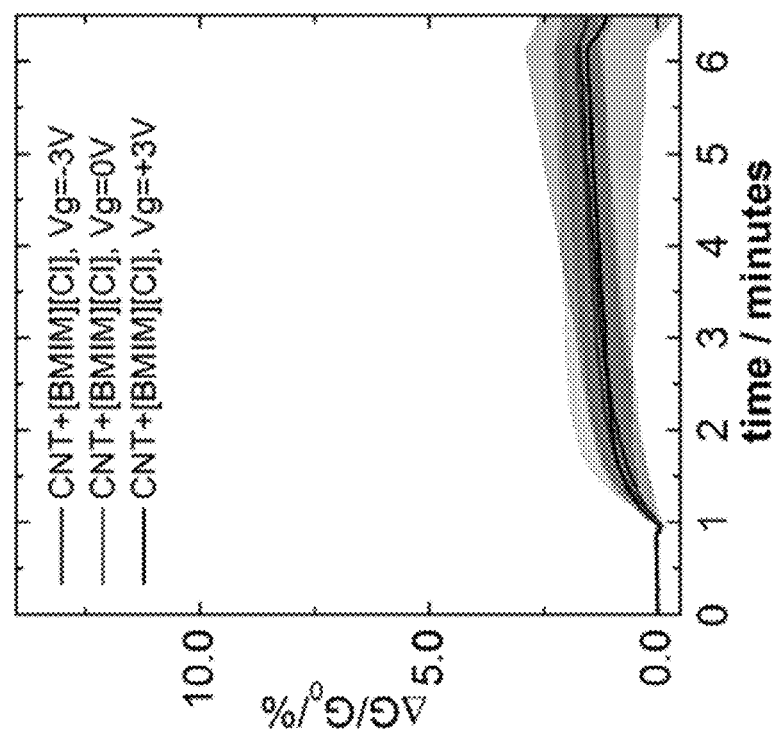
FIG. 35 depicts properties of a sensor.
Figure 36:
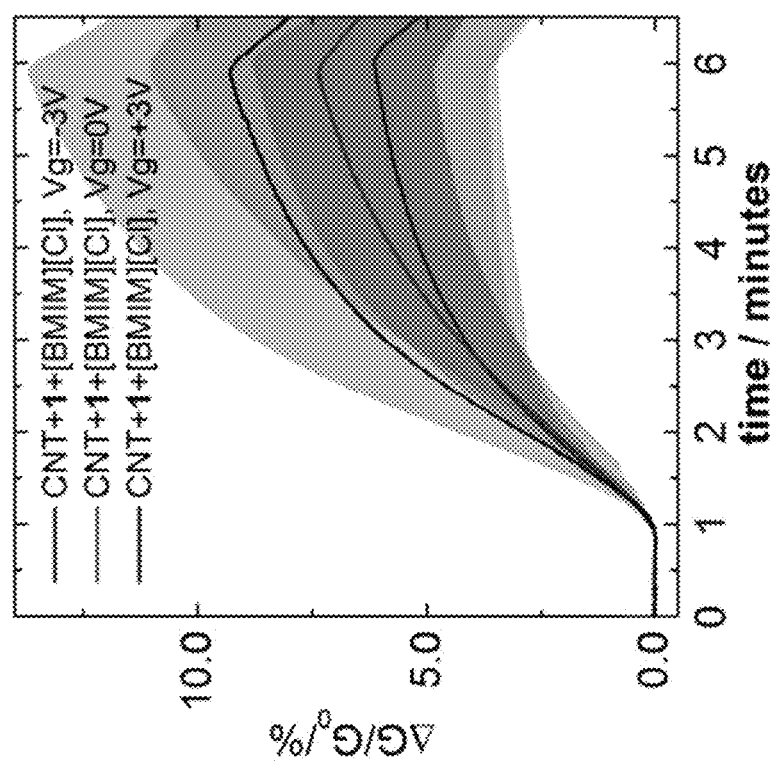
FIG. 36 depicts properties of a sensor.

Referring to FIGS. 35 and 36, experiments were conducted including ionic liquid matrix 1-Butyl-3-methylimidazolium chloride ([BMIM][Cl]) to improve reactivity on device. Increased response from a 1-device was observed, albeit with no improvement with gate voltage.

The following references cited above are incorporated by reference in their entirety.

1. J. A. Raub, M. Mathieu-Nolf, N. B. Hampson, S. R. Thom, *Toxicology* 2000, 145, 1-14.
2. Occupational Safety and Health Administration, "Carbon Monoxide In Workplace Atmospheres (Direct-Reading Monitor)," 1993.
3. F. J. Gonzales, *Pharmacol. Rev.* 1985, 40, 243-288.
4. M. Klingenberg, *Arch. Biochem. Biophys.* 1958, 75, 376-386.
5. R. Omura, Tsuneo; Sato, *J. Biol. Chem.* 1964, 239, 2370-2378.
6. M. F. Perutz, *Annu. Rev. Physiol.* 1990, 52, 1-25.
7. A. Rossi-Fanelli, E. Antonini, *Arch. Biochem. Biophys.* 1958, 77, 478-492.
8. Stephen R. Thom, *N Engl J Med* 2002, 347, 1105-1106.
9. Stephen R. Thom, L. W. Keim, Clin. *Toxicol.* 989, 27, 141-156.
10. J. F. F. Jr, S. F. Liu, M. Joseph, J. G. Weis, S. Rochat, K. A. Mirica, J. B. Ravnsbak, T. M. Swager, n.d.
11. J. E. Ellis, A. Star, *Chempluschem* 2016, 81, 1248-1265.
12. L. Torsi, M. Magliulo, K. Manoli, G. Palazzo, *Chem. Soc. Rev.* 2013, 42, 8612.
13. S. F. Liu, A. R. Petty, G. T. Sazama, T. M. Swager, *Angew. Chemie* Int. Ed. 2015, 54, 6554.
14. A. Star, J. C. P. Gabriel, K. Bradley, G. Gruner, *Nano Lett.* 2003, 3, 459-463.
15. R. P. Deo, J. Wang, I. Block, A. Mulchandani, K. A. Joshi, M. Trojanowicz, F. Scholz, W. Chen, Y. Lin, *Anal. Chim. Acta* 2005, 530, 185-189.
16. B. Esser, J. M. Schnorr, T. M. Swager, *Angew. Chemie—Int. Ed.* 2012, 51, 5752-5756.
17. M. Dionisio, J. M. Schnorr, V. K. Michaelis, R. G. Griffin, T. M. Swager, E. Dalcanale, *J. Am. Chem. Soc.* 2012, 134, 6540-6543.
18. S. Santucci, S. Picozzi, F. Di Gregorio, L. Lozzi, C. Cantalini, L. Valentini, J. M. Kenny, B. Delley, *J. Chem. Phys.* 2003, 119, 10904-10910.
19. D. Fu, H. Lim, Y. Shi, X. Dong, S. G. Mhaisalkar, Y. Chen, S. Moochhala, L. Li, *J. Phys. Chem. C* 2008, 112, 650-653.
20. D. R. Kauffman, A. Star, *Angew. Chem. Int. Ed. Engl.* 2008, 47, 6550-6570.
21. L. B. Da Silva, S. B. Fagan, R. Mota, *Nano Lett.* 2004, 4, 65-67.
22. S. Peng, K. J. Cho, *Nano Lett.* 2003, 3, 513-517.
23. Y. Wanna, N. Srisukhumbowornchai, A. Tuantranont, A. Wisitsoraat, N. Thavarungkul, P. Singjai, *J. Nanosci. Nanotechnol.* 2006, 6, 3893-3896.
24. A. Star, V. Joshi, S. Skarupo, D. Thomas, J.-C. P. Gabriel, *J. Phys. Chem. B* 2006, 110, 21014-21020.
25. O. K. Varghese, P. D. Kichambre, D. Gong, K. G. Ong, E. C. Dickey, C. A. Grimes, *Sensors Actuators B* 2001, 81, 32-41.
26. S. Chopra, K. McGuire, N. Gothard, A. M. Rao, A. Pham, *Appl. Phys. Lett.* 2003, 83, 2280-2282.
27. S. F. Liu, S. Lin, T. M. Swager, *ACS Sensors* 2016, 1, 354-357.
28. X. Dong, D. Fu, M. O. Ahmed, Y. Shi, S. G. Mhaisalkar, S. Zhang, S. Moochhala, X. Ho, J. A. Rogers, L. J. Li, *Chem. Mater.* 2007, 19, 6059-6061.
29. L. Que, W. B. Tolman, *Nature* 2008, 455, 333-340.
30. W. B. Tolman, *Inorg. Chem.* 2013, 52, 7307-7310.
31. M. C. De La Torre, M. A. Sierra, *Angew. Chemie—Int. Ed.* 2003, 43, 160-181.
32. S. J. Lippard, J. M. Berg, *Principles of Bioinorganic Chemistry*, University Science Books, Mill Valey, California, 1994.
33. Y. He, J. Zhang, J. Zhao, *J. Phys. Chem. C* 2014, 118, 18325-18333.
34. T. Shimizu, D. Huang, F. Yan, M. Stranava, M. Bartosova, V. Fojtikova, M. Martinkova, *Chem. Rev.* 2015, 115, 6491-6533.
35. M. He, T. M. Swager, *Chem. Mater.* 2016, 28, 8542-8549.
36. S. Paul, F. Amalraj, S. Radhakrishnan, *Synth. Met.* 2009, 159, 1019-1023.
37. W. Maser, E. M. Benito, E. Mufioz, M. T. Martinez, *Functionalized Nanoscale Materials, Devices and Systems*, Springer, Dordrecht, 2008.
38. S. Banerjee, T. Hemraj-Benny, S. S. Wong, *Adv. Mater.* 2005, 17, 17-29.
39. L. Liu, K. C. Etika, K. S. Liao, L. A. Hess, D. E. Bergbreiter, J. C. Grunlan, *Macromol. Rapid Commun.* 2009, 30, 627-632.
40. C. Rovira, P. Ballone, M. Parrinello, *Chem. Phys. Lett.* 1997, 271, 247-250.
41. L. M. Blomberg, M. R. A. Blomberg, P. E. M. Siegbahn, *J. Inorg. Biochem.* 2005, 99, 949-958.
42. A. Abdurahman, T. Renger, *J. Phys. Chem. A* 2009, 113, 9202-9206.
43. J. A. Bailey, *J. Chem. Educ.* 2011, 88, 995-998.
44. D. R. Kauffman, O. Kuzmych, A. Star, *J. Phys. Chem. C* 2007, 111, 3539-3543.
45. G. Balducci, G. Chottard, C. Gueutin, D. Lexa, J.-M. Saveant, *Inorg. Chem.* 1994, 33, 1972-1978.
46. Z. Zanolli, R. Leghrib, A. Felten, J. J. Pireaux, E. Llobet, J. C. Charlier, *ACS Nano* 2011, 5, 4592-4599.
47. Q. Wang, Y. Tong, X. Xu, *Struct. Chem.* 2015, 26, 815-822.
48. W. L. Yim, Z. F. Liu, *Chem. Phys. Lett.* 2004, 398, 297-303.
49. M. Penza, M. Alvisi, R. Rossi, E. Serra, R. Paolesse, a D'Amico, C. Di Natale, *Nanotechnology* 2011, 22, 125502.

Examples

1. Experimental Methods

A. Materials and Instrumentation

SWCNTs used in this work was purified SWCNTs with (7,6) chirality with >90% carbon content and >77% carbon as SWCNTs (0.7-1.1 nm diameter) purchased from Aldrich. Commercially available solvents-dichloromethane (DCM), 1,2-dichlorobenzene (o-DCB), acetone, tetrahydrofuran <0.025% butylated hydroxytoluene as inhibitor, isopropyl alcohol-were purchased from Sigma-Aldrich and used as received. Carbon monoxide (1%), carbon dioxide (100%), oxygen (100%), and pressurized air were purchased from Airgas. Iron porphyrin, Fe(tpp)ClO$_4$, was synthesized according to literature procedure. Refs. 1A and 2A. SWCNTs were covalently functionalized according to a previously reported method. Ref. 3A. Briefly, SWCNTs were readily reduced in situ with sodium naphthalide at room temperature, followed by the addition of pyridyl iodonium salts.

Characterizations of the pyridyl-functionalized SWCNTs (F-SWCNTs) were performed using thermogravimetric analysis/mass spectrometry (TGA-MS), Raman spectroscopy, ultraviolet-visible-near infrared (UV-Vis-NIR) spectrophotometer, and X-ray photoelectron spectroscopy (XPS) as outlined previously. Ref 3A. TGA-MS was performed with a TA Discovery TGA system coupled to a Pfeiffer vacuum mass spectrometer. Raman spectra were taken with a Horiba Jobin-Yvon LabRam (Model HR 800) Raman confocal microscope with 785 nm laser excitation and the laser spot size of 1.7 m. Ultraviolet-visible absorption spectra were collected on a Cary 4000 UV-visible spectrophotometer and corrected for background signal with a solvent filled cuvette. UV-Vis-NIR absorption spectra were measured in quartz cuvettes using an Agilent Cary 5000 UV-Vis-NIR spectrophotometer. XPS measurement were performed on a Physical Electronics Versaprobe II XPS spectrometer with a hemispherical energy analyzer and a monochormated X-ray source (Al Kα, 1486.6 eV). Differential pulse voltammetric responses were recorded on a Bio-Logic VSP potentiostat in phosphate buffer (0.050 M $KH_2PO_4$, 0.050 M $K_2HPO_4$ in ultrapure water) using a three-electrode system consisting of a Pt-wire counter electrode, Ag/AgCl reference electrode, and glassy carbon working electrode. The carbon nanomaterial was drop-casted from a dispersion in ortho-dichlorobenzene on the glassy carbon electrode and infused with Fe(tpp)$ClO_4$ via submersion in a 1 mg m$^{-1}$ solution in dichloromethane for 5 minutes. DPV were recorded with a 2.5 mV pulse height, a 100.0 ms pulse width, a step height of −5.0 mV, and a step time of 500.0 ms at an overall scan rate of −10.000 mV s$^{-1}$. Scanning electron microscope (SEM) images were obtained using a JEOL 6010LA SEM with an accelerating voltage of 15 kV.

B. Fabrication of Sensors

Sensors were prepared on field-effect transistor-based substrates with a bottom gate, bottom contact configuration. Heavily p++ doped silicon wafers were used as the common gate with 300 nm of $SiO_2$ grown on top acting as the dielectric layer. The source and drain electrodes (10 nm Ti and 100 nm Au) were photolithographically patterned on the $SiO_2$ surfaces with a channel length and width of L=200 µm and W=3 mm, respectively. The patterned substrates were cleaned by bath sonication in DI water, acetone, IPA, and dried under an $N_2$ flow. In a typical device, the sensors were prepared by two-step deposition of F-SWCNTs via drop-casting and infusion of Fe(tpp)$ClO_4$. Functionalized SWCNTs were suspended in o-DCB at the concentration of 0.25 mg mL$^{-1}$ and drop-casted onto the patterned substrates between the source/drain channels using a micropipette. Each substrate contained four identical channels. The solvent was removed in vacuo. The drop-casting was repeated until the resistance across the electrodes reached a resistance of 1-10 kΩ as measured by a multimeter. Subsequently, the substrates with F-SWCNTs were then submerged in a solution of Fe(tpp)$ClO_4$ in DCM at the concentration of 1 mg mL$^{-1}$ for 1 min and dried under $N_2$ flow. For comparison, one-step drop-casting of the mixture of F-SWCNTs and Fe(tpp)$ClO_4$ in o-DCB at the concentration of 0.25 mg mL$^{-1}$ F-SWCNTs and 0.75 mg mL$^{-1}$ Fe(tpp)$ClO_4$ was used on separate substrates.

C. Gas Detection Measurement

Gas detection measurements were performed by placing the sensors into a custom built PTFE enclosure with a small gas inlet and outlet. Device test clip (3M) provided the electrical contacts between the source/drain electrodes and the gate (FIGS. 15A-15D). PalmSens EmStat potentiostat equipped with a MUX16 multiplexer was used to apply the source-drain voltage (0.100 V) and measure the conductance across the source/drain electrodes. The gate voltage was control by a Keithley 2450 source-measure unit. The analyte gas and the carrier gas ($N_2$ or air) were delivered to the enclosure using two digital mass flow controllers (MFCs) purchased from Alicat Scientific.

FIGS. 15A-15D show: (a) a photograph of the experimental gas sensing setup showing the mass flow controllers and gas enclosure, (b) a photograph of sensor connected to the test clip outside of the PTFE gas enclosure, (c) a photograph of the sensing setup showing a more detailed view of the Alicat Scientific mass flow controllers and (d) a photograph of the PTFE gas enclosure showing the gas inlet and outlet.

2. Characterization of Functionalized SWCNTs

Pyridyl-functionalized CNTs (F-SWCNTs) were fabricated and characterized according a previous report.[3] The density of functionalization or the number of pyridyl group per 100 atoms of carbon of the SWCNTs were calculated using the equation below:

$$DF = \frac{(A_{wt-loss} - N_{wt-loss})/A_{MW}}{R_{wt}/C_{MW}} \times 100 \qquad \text{(eq. 1)}$$

Where DF is the degree of functionalization, as defined by the number of addend per 100 carbon atoms of SWCNTs. $A_{wt-loss}$ is the TGA weight loss of functionalized CNTs at 500° C., $N_{wt-loss}$ is the TGA weight loss of pristine SWCNTs at 500° C. $A_{MW}$ is the molecular weight of addend, $R_{wt}$ is the residual weight of the sample, and $C_{MW}$ is the molecular weight of carbon (12 g mol$^{-1}$).

The reaction scheme and the conditions are reported in FIG. 3 and Table S1. The F-SWCNTs s were characterized via Raman spectroscopy, TGA, XPS, and UV-Vis-NIR, (FIGS. 7A-7D and Table S2).

From previously published results, it has been determined that the more electron-withdrawing aryl groups (such as the pyridyl group) are preferentially transferred onto the sidewall of the SWCNTs. Ref. 3A. Additionally, sterically unencumbered groups are transferred preferentially when compared to sterically congested groups. Based on these design principles, we chose the asymmetric iodonium group containing triisopropylphenyl and pyridyl to maximize the ratio of pyridy groups that can get transferred onto the SWCNT sidewall. The use of an asymmetric iodonium salt is discussed previously in Ref. 35 (main text): "Unsymmetrical diaryliodonium salts bearing two different aryl groups on the iodine atom have been used widely in organic synthesis as arylating agents. One advantage is that, by using a "spectator" arene that does not transfer, only one equivalent of the arene of interest is required." Ref. 3A.

The specificity of the iodonium reagent used in this study was analyzed by investigating the presence of the byproducts of the functionalization reaction in the filtrate of the synthesis, FIG. 4. A ratio of 1:3.1:1.3 for the byproducts 4-iodopyridine, 1-iodo-2,4,6-triisopropylbenzene, and 1,3,5-triisopropylbenzene was found. The large difference between the amount of 1-iodo-2,4,6-triisopropylbenzene when compared to 4-iodopyridine in the filtrate indicates that a majority of the pyridyl groups reacted with the SWCNT. Furthermore, the presence of 1,3,5-triisopropylbenzene is an indication that steric hindrance impeded the transfer of this group with the SWCNTs.

FIG. 3 shows reaction of pyridyl-iodonium salt with pristine SWCNTs.

TABLE S1

Reaction conditions used to functionalize SWCNTs.

|         | (7,6) SWCNT (equiv) | Sodium naphthalide (equiv) | Iodonium salt (equiv) | # of pyridine group per 100 C atoms |
|---------|---------------------|----------------------------|-----------------------|-------------------------------------|
| f-CNT-1 | 1                   | 0.05                       | 0.05                  | 1.4                                 |
| f-CNT-2 | 1                   | 0.1                        | 0.1                   | 1.9                                 |
| f-CNT-3 | 1                   | 0.2                        | 0.2                   | 2.0                                 |

FIGS. 7A-7D show characterizations of functionalized SWCNTs: (a) Raman spectroscopy, (b) TGA, (c) XPS, and (d) UV-Vis-NIR.

TABLE S2

Summary of X-ray photoelectron spectroscopy (XPS) analysis of pristine SWCNTs and functionalized SWCNTs used in this paper.

|                | C 1s | O 1s | F 1s | N 1s |
|----------------|------|------|------|------|
| Pristine SWCNTs | 94.0 | 5.2  | 0.8  | 0    |
| F-SWCNT-1      | 95.0 | 4.3  | 0    | 0.7  |
| F-SWCNT-2      | 94.3 | 4.2  | 0    | 1.5  |
| F-SWCNT-3      | 94.5 | 3.8  | 0    | 1.7  |

FIG. 4 shows an $^1$H NMR spectrum of the reaction filtrate of a functionalization of SWCNTs using 0.05 equivalents of sodium naphtalide and 0.05 equivalents of the pyridyl iodononium salt measured in in CDCl$_3$.

3. Scanning Electron Microscopy (SEM) Experiments

From the SEM images, the optimal method of device fabrication was determined. Initially, the F-SWCNTs and Fe(tpp)ClO$_4$ were co-dissolved in o-DCB and drop-casted between the electrodes. However, it was observed that the devices fabricated from a mixed solution resulted in large crystallites of the iron porphyrin and poor uniformity of the films, FIGS. 16A-16B. These devices also suffer from large variations between samples. Thus, a two-step fabrication process described above was implemented in which the dispersion of F-SWCNTs were drop-cast first then infused the iron porphyrin in a second step. FIG. 16C shows the surface between the electrode comprising of purely F-SWCNTs and FIG. 16D shows the same surface after infusing with iron porphyrin. The devices fabricated from the two-step method resulted in a much more uniform deposition of iron porphyrin and less variations from sample to sample.

FIGS. 16A-16D show SEM images of the devices comprising F-SWCNTs and iron porphyrin. (a) Devices fabricated by a one-step method of drop-casting a mixed solution of F-SWCNTs and Fe(tpp)ClO$_4$ and a magnified image (b). (c) Surface of pure F-SWCNTs before infusion of Fe(tpp)ClO$_4$ (d).

4. Differential Pulse Voltammetry (DPV) Experiments

Figure 6A:
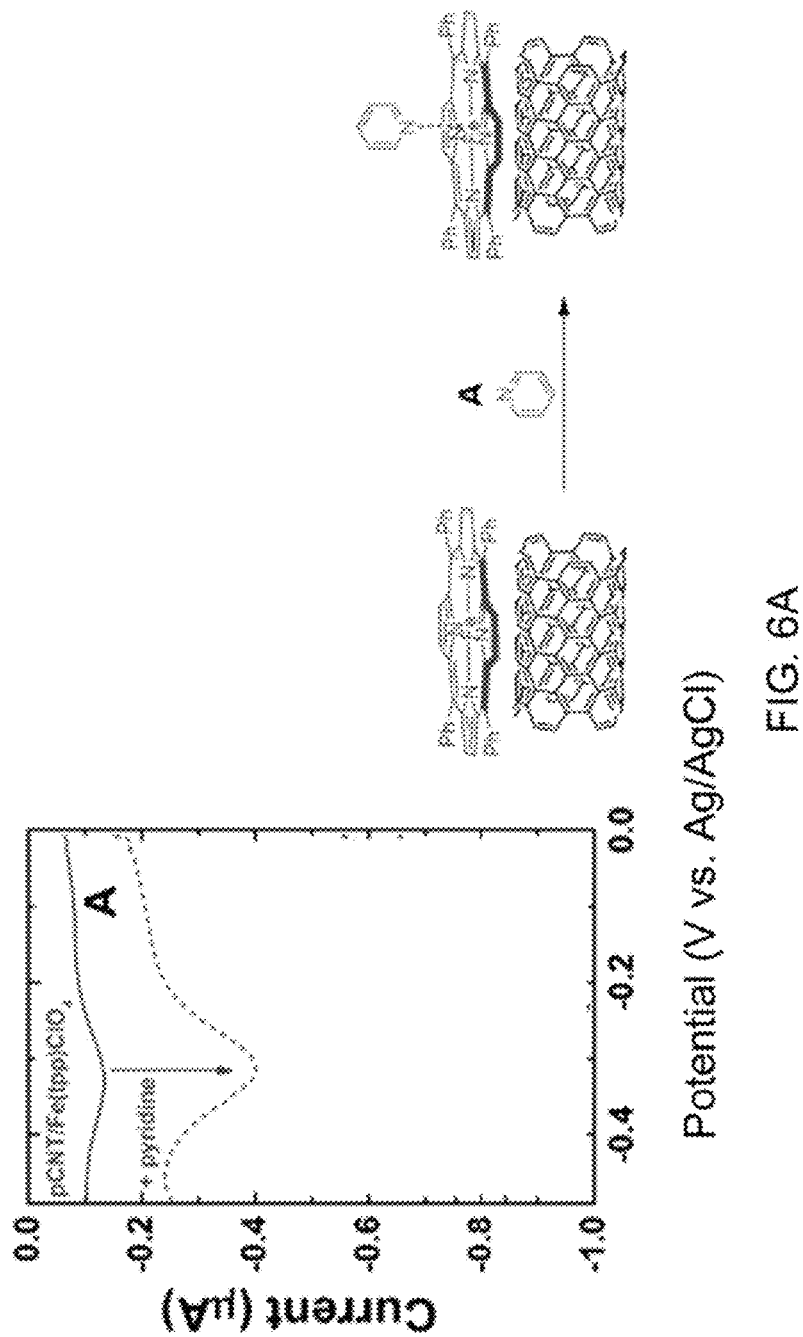
FIGS. 6A-6D depict properties of a sensor.
Figure 6B:
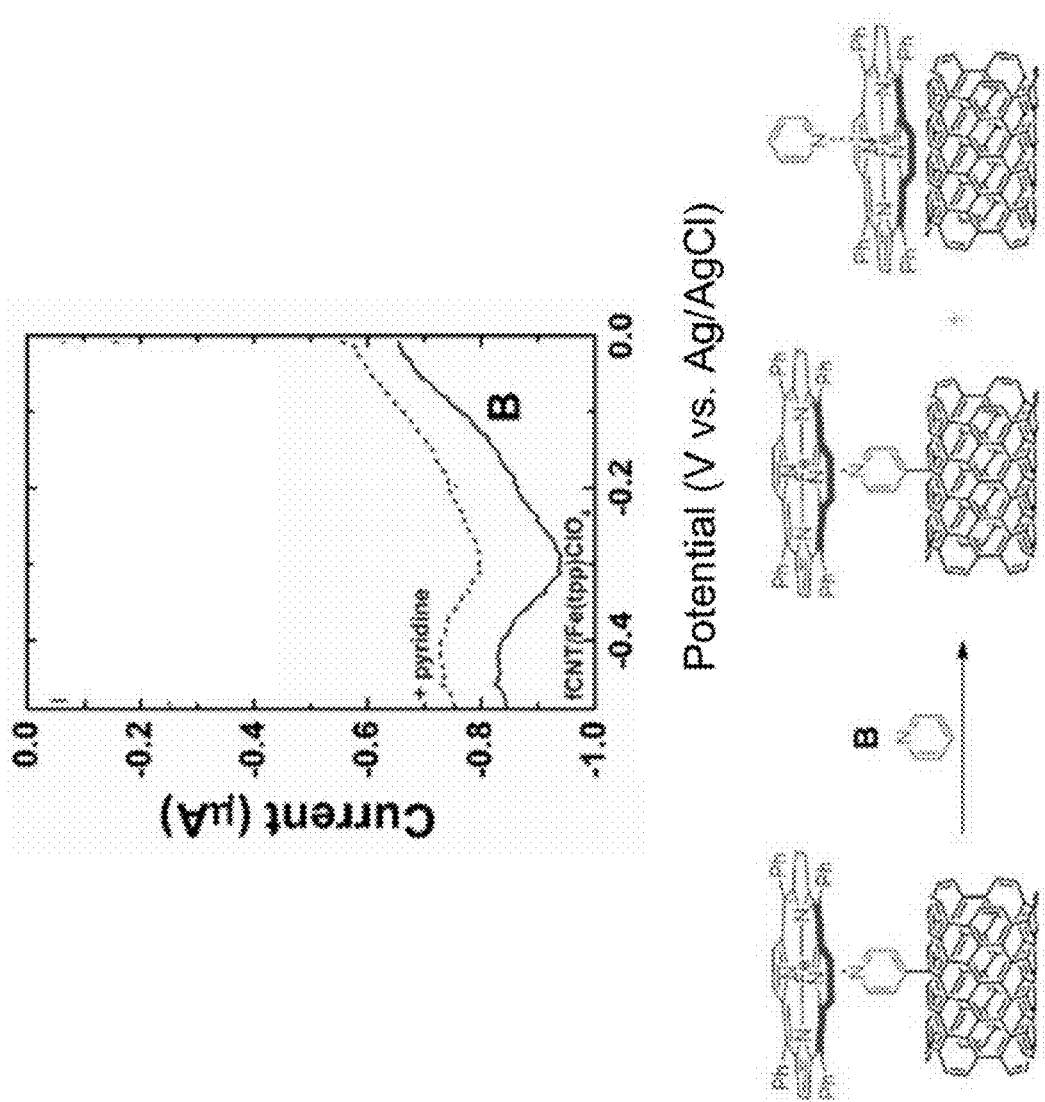
Figure 6C:
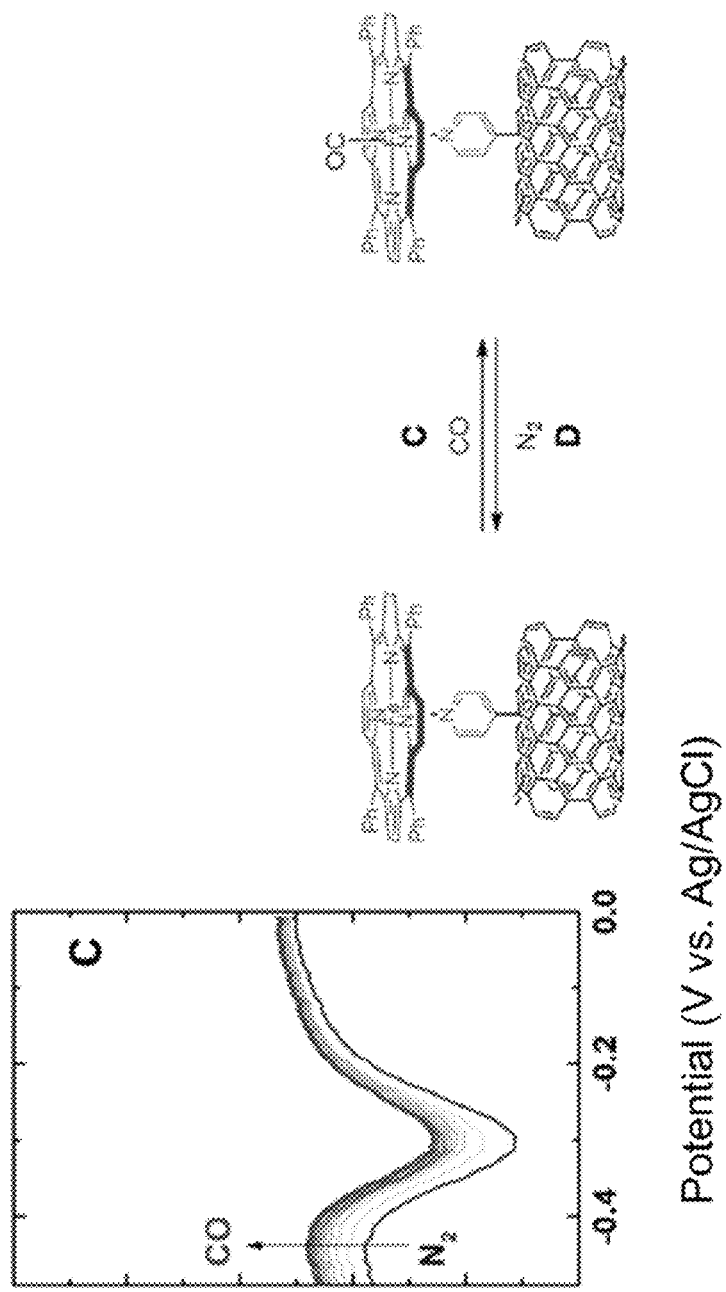
Figure 6D:
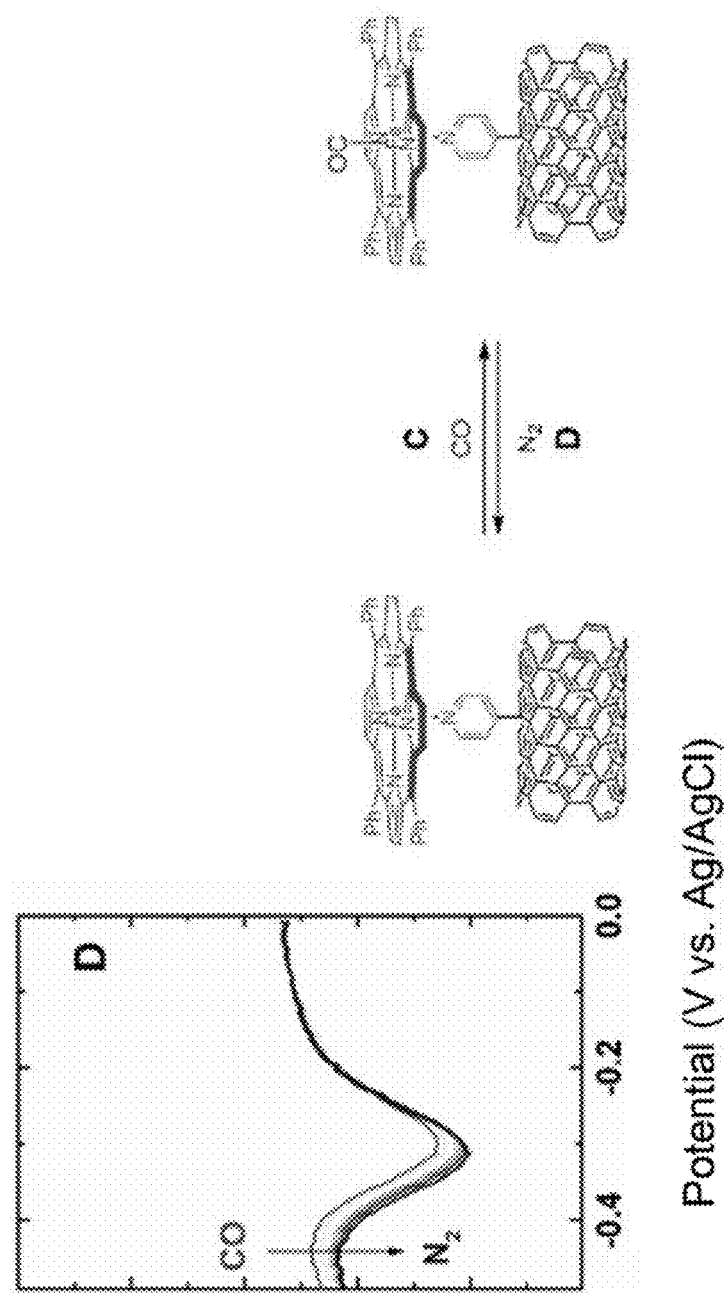

The redox behavior of electrode-adsorbed Fe(tpp)ClO$_4$-decorated SWCNTs electrochemically under N$_2$ atmosphere was observed. While cyclic voltammetry experiments yielded little signal relative to noise, differential pulse voltammetry (DPV) proved to be a more sensitive and useful technique. The reduction wave observed at −0.3 V increased strongly in intensity upon the addition of pyridine for pristine SWCNTs decorated with Fe(tpp)ClO$_4$ (FIG. 6A) while no such increase was observed for the identical experiment using functionalized CNTs decorated with Fe(tpp)ClO$_4$ (FIG. 6B). This reduction event was attributed to the reduction of Fe$^{II}$ tethered to a pyridyl unit. FIG. 6C shows a decrease of intensity of this event upon exposure to CO and FIG. 16D shows a slight recovery of the signal upon purging with N$_2$ over night. The Fe$^{III}$/Fe$^{II}$ wave reduction observed at −0.3 V decreases in intensity due to the strong relative stabilization of the Fe$^{II}$ complex against the Fe$^{III}$ complex caused by the strong binding of CO. Ref 4. These findings support a hypothesis that Fe(tpp)ClO$_4$ can be reduced in situ while anchored to a SWCNT and that it can react with CO.

FIGS. 6A-6D Differential pulse voltammetry under N$_2$ and schematic explanation of processes during DPV experiment. (A) DPV of pristine SWCNTs decorated with Fe(tpp) ClO$_4$ before and after addition of pyridine. (B) DPV of functionalized SWCNTs decorated with Fe(tpp)ClO$_4$ before and after addition of pyridine. (C) DPV of functionalized SWCNTs decorated with Fe(tpp)ClO$_4$ before and at certain points during exposure to CO. (D) DPV of functionalized SWCNTs decorated with Fe(tpp)ClO$_4$ under CO before and at certain points during purging with N$_2$.

5. Supplemental Sensing Experiments

A. Comparison to Detector Standard

The selector enables has sufficient sensitivity and response time to meet the standards for sensitivity towards CO exposure and response time as set by the 'Standard for Single and Multiple Station Carbon Monoxide Alarms" provided by Underwriters Laboratories (UL 2034) (Ref. 5):

TABLE S3

UL2034 Required Alarm Points for different levels of CO.

| Concentration (ppm) | Response time (min) | Can be targeted with the sensor |
|---------------------|---------------------|--------------------------------|
| 100                 | less than 90        | yes                            |
| 200                 | less than 35        | yes                            |
| 400                 | less than 15        | yes                            |

B. Change in Conductance from Long Exposure and Various Concentration of CO

Figure 17:
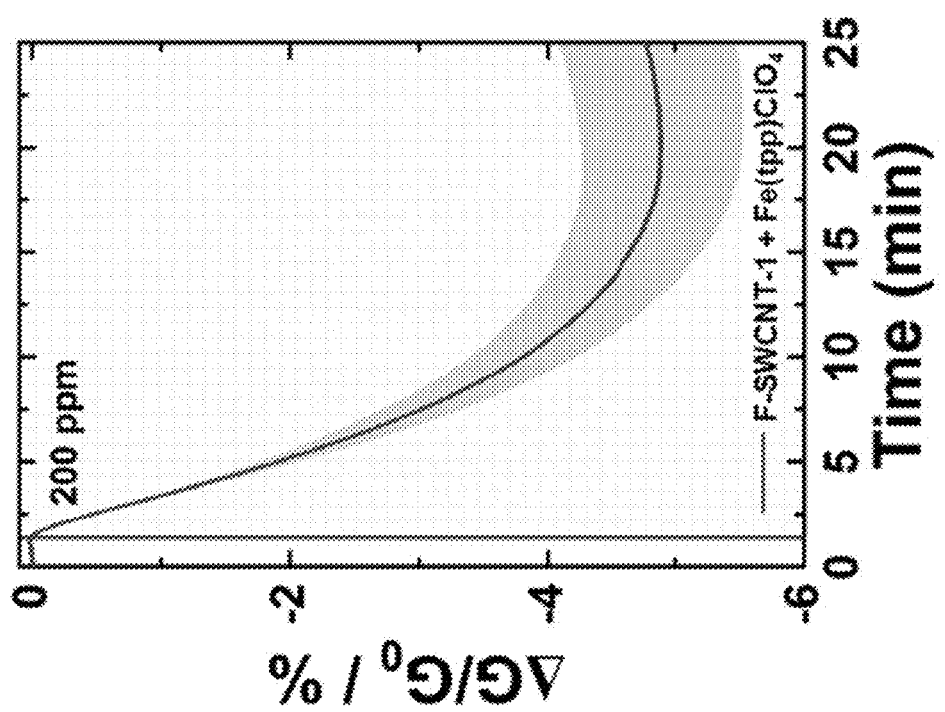
FIG. 17 depicts properties of a sensor.

FIG. 17 show a trace of the change in conductance of the CO sensors with prolonged exposure to 200 ppm of CO. A deviation from the linear response occurred near 10 min and the saturated regime was observed after 15 min.

Figure 18:
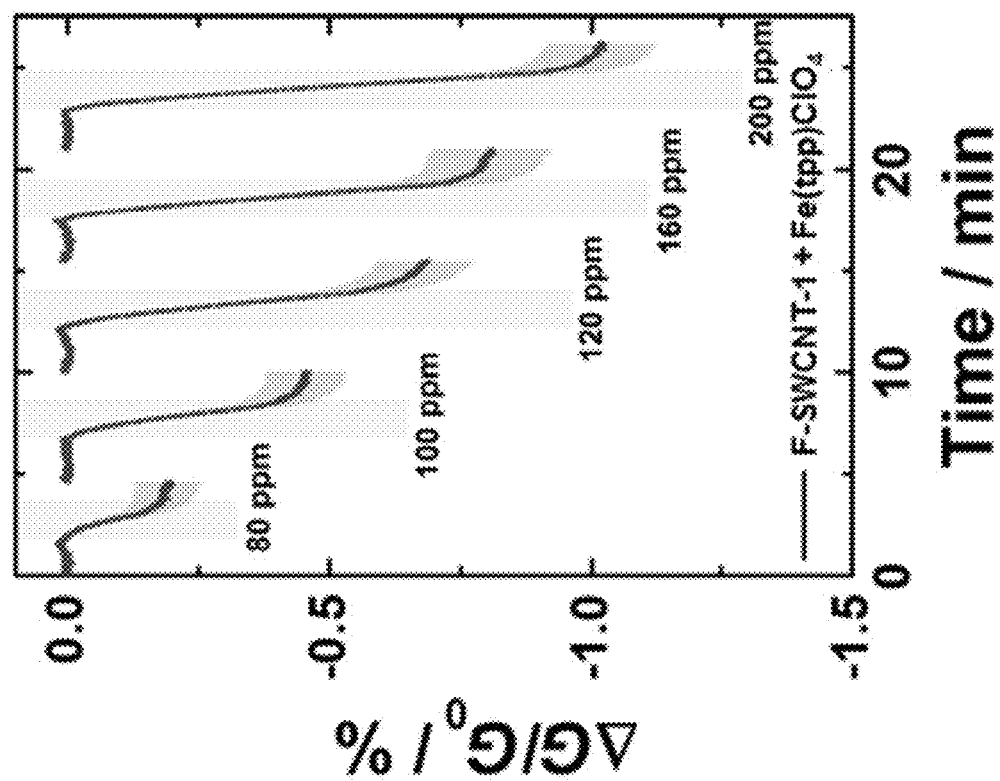
FIG. 18 depicts properties of a sensor.

FIG. 18 shows conductance changes of F-SWCNT-1 with Fe(tpp)ClO$_4$ in response to various concentrations of CO gas diluted in N$_2$.

6. UV-Vis Spectra of Fe(Tpp)ClO$_4$ in THF Solution

FIGS. 10A-10F show a UV-Vis investigation of reactivity of Fe(tpp)ClO$_4$ in THF solution (1 μM). (a) UV-Vis spectra of Na-reduced species before and at various times after purging with air to demonstrate aerobic reoxidation. (b) UV-Vis spectra of fully reduced porphyrin upon addition of CO before and after vortexing in air for 15 min to show irreversibility of the binding of CO. (c) UV-Vis spectra of Fe(tpp)ClO$_4$ as-is before and after various times of vortexing in air. FIG. 18 shows the same samples as FIG. 9A in the range of 450-600 nm. (d) UV-Vis spectra (450 nm to 600 nm) of Fe(tpp)ClO$_4$ before and at various times after addition of Na metal. (e) UV-Vis spectra (450 nm to 600 nm) of fully reduced porphyrin upon addition of CO before and after vortexing in air for 15 min. (f) UV-Vis spectra (450 nm to 600 nm) of Fe(tpp)ClO$_4$ as-is before and after various times of vortexing in air.

7. Computational Methods

Four different structures were selected to illuminate the sensing mechanism (FIG. 13). The SWCNT fragment contains 110 carbon atoms. All quantum chemical calculations were carried out with the Gaussian 09 program package. Ref. 6. The molecular geometries were optimized using density functional theory (DFT) with a two-layer ONIOM approach. Ref. 7. The porphyrin unit and a 32-carbon-containing piece of the SWCNT underneath the porphyrin were treated with hybrid meta-GGA functional ωB97XD containing empirical dispersion terms and long-range corrections with the 6-31G basis set without symmetry constraints. The remaining piece of the carbon nanotube was treated semi-empirically using the PM6 method. Refs. 8-11. Effects from solvent were not taken into account. Subsequently, single-point calculations were performed in which the complete model was treated using DFT/ωB97XD 6-31G. Multiwfn was used to generate the total density-of-states (with Gaussian broadening, full width at half maximum=0.300 eV), Fermi energy and atomic charges. Ref 12. ChemCraft was used to generate 3D representation of molecules and molecular orbitals. Ref. 13.

As in the software program Multiwfn, in this report, Fermi levels are determined as the highest occupied molecular orbital (HOMO) energy levels. Although not exact, this approximation enables illustration of the electronic effect of CO binding with relatively simple DFT calculations. (1) HOMO energy level is related to the first vertical ionization potential by the DFT analogue of Koopman's theorem— while not exact, this approximation is fairly accurate for long-range corrected functionals such as ωB97DX. Refs. 14 and 15. (2) For polycyclic aromatic hydrocarbons, DFT-calculated HOMO energies have good linear correlation with experimental oxidation potentials. Ref. 16. And (3) for small molecules, redox potentials can be interpreted as identical, except for reference level, to Fermi levels. Ref 17A.

FIG. 13 shows ground-state geometries of (5,5) SWCNT fragment (a) pristine, (b) with a Fe$^{II}$ porphyrin, and with small gaseous ligands: CO (c), and O$_2$ (d). Schematic illustrating the high and low level of the ONIOM calculation of (5,5) SWCNT fragment (e) pristine, (f) with a Fe$^{II}$ porphyrin, and with small gaseous ligands: CO (g), and O$_2$ (h).

Figure 19:
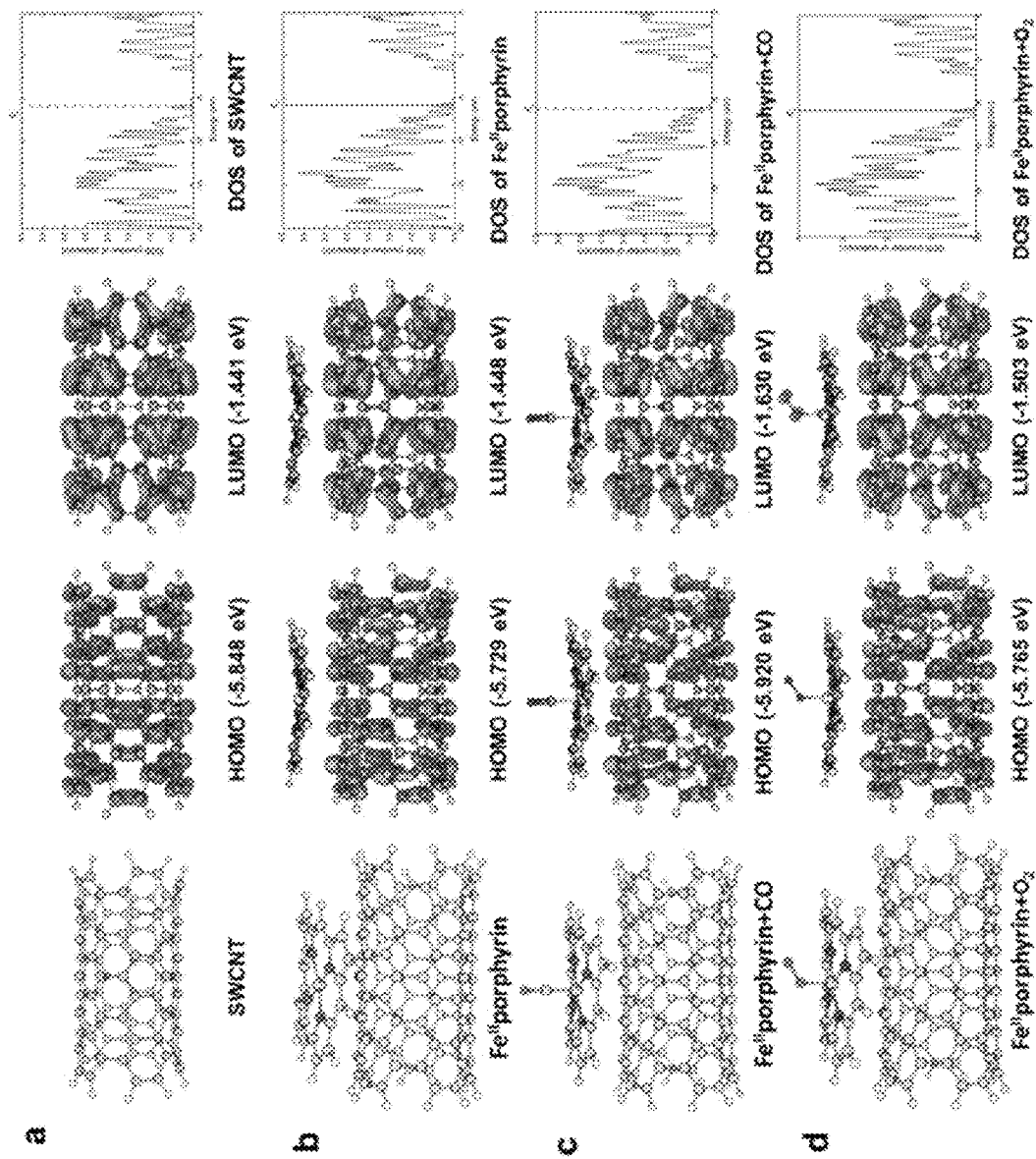
FIG. 19 depicts properties of a carbon material.

FIG. 19 shows frontier orbitals (contour value=0.02 e/a.u.$^3$) and DOS for pristine (5, 5) SWCNT (a), (5, 5) SWCNT with Fe$^{II}$ porphyrin (b), (5, 5) SWCNT with Fe$^{II}$ porphyrin and CO (c), and (5, 5) SWCNT with Fe$^{II}$ porphyrin and O$_2$.

Figure 20:
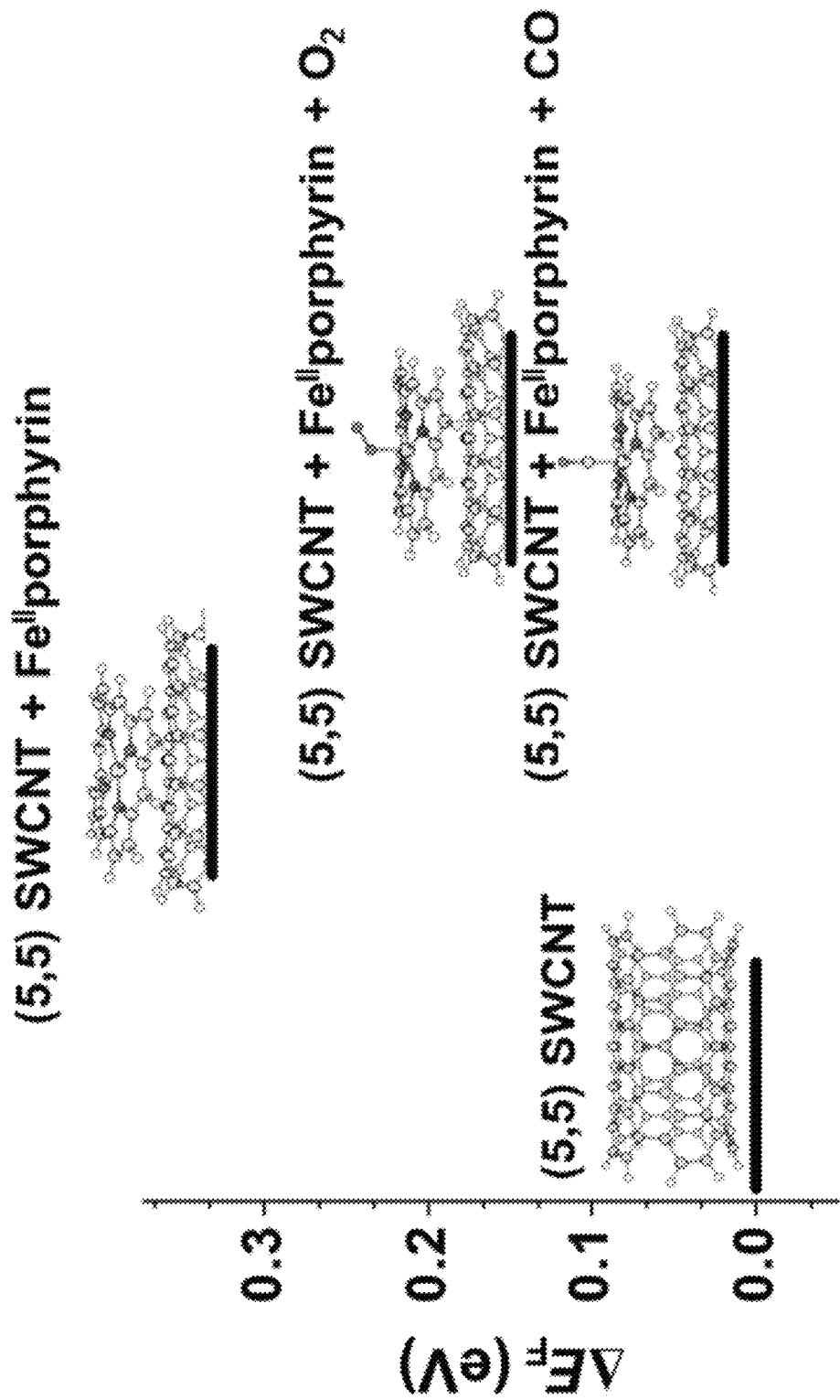
FIG. 20 depicts properties of a carbon material.

FIG. 20 shows computed change in the Fermi energy ($\Delta E_F$) of the ONIOM calculation upon addition of Fe$^{II}$ porphyrin and subsequent addition of CO or O$_2$ relative to the Fermi energy of the pristine SWCNT with inserts of the ground-state geometries.

TABLE S4

Fe-SWCNT bond lengths ($d_{Fe-cNT}$, Å), Fe-gas bond lengths ($d_{Fe-L}$, Å), and Fermi level ($E_{Fermi}$, eV), binding angle between Fe and ligand (∠Fe—CO/O, °).

|  | (5,5) SWCNT | Fe$^{II}$porphyrin | Fe$^{II}$porphyrin CO | Fe$^{II}$porphyrin O$_2$ |
|---|---|---|---|---|
| $d_{Fe-CNT}{}^a$ | — | 2.70 | 3.15 | 3.23 |
| $d_{Fe-L}$ | — | — | 1.72 | 1.93 |
| $\Delta E_{Fermi}{}^b$ | 0 | 0.332 | 0.02 | 0.15 |
| ∠Fe—CO/OO | — | — | 180.0 | 121.9 |

$^b$Distance between the Fe atom and the surface of the SWCNT
$^c$Maximum of the Valence orbitals relative to the pristine SWCNT

TABLE S5

Atomic dipole moment corrected Hirshfeld population, and Becke (Ref. 18A) charges on (5,5) SWCNT, (5,5) SWCNT and Fe$^{II}$porphyrin, (5,5) SWCNT and Fe$^{II}$porphyrin and CO, and (5,5) SWCNT and Fe$^{II}$porphyrin and O$_2$.

|  | Fe$^{II}$porphyrin | Fe$^{II}$porphyrin CO | Fe$^{II}$porphyrin O$_2$ |
|---|---|---|---|
| ADCH | | | |
| $\Delta q_{CNT}$ | 0.0688 | 0.137 | 0.0518 |
| $\Delta q_{FeIIporphyrin}$ | −0.0688 | −0.267 | 0.207 |
| $\Delta q_{Ligand}$ | — | 0.130 | −0.259 |
| Becke | | | |
| $\Delta q_{CNT}$ | 0.112 | 0.376 | 0.0807 |
| $\Delta q_{FeIIporphyrin}$ | −0.112 | −0.743 | −0.0186 |
| $\Delta q_{Ligand}$ | — | 0.366 | −0.0627 |

8. Transfer Characterizations of Functionalized SWCNTs

FIG. 12 shows transfer characteristic of P-SWCNT, F-SWCNT-1, and F-SWCNT-1+Fe(tpp)ClO$_4$ with the constant drain-source voltage of 0.1 V.

The following references for this second section are each incorporated by reference in their entirety.

1A. S. F. Liu, L. C. H. Moh, T. M. Swager, Chem. Mater. 2015, 27, 3560-3563.
2A. W. R. Scheidt, I. A. Cohen, M. E. Kastner, Biochemistry 1979, 18, 3546-3552.
3A. M. He, T. M. Swager, Chem. Mater. 2016, 28, 8542-8549.
4A. G. Balducci, G. Chottard, C. Gueutin, D. Lexa, J.-M. Saveant, Inorg. Chem. 1994, 33, 1972-1978.
5A. Underwriters Laboratories, Single and Multiple Station Carbon Monoxide Alarms—UL 2034, Underwriters' Laboratories, Northbrook, IL, 2005.
6A. G. E. S. M. J. Frisch, G. W. Trucks, H. B. Schlegel, B. M. M. A. Robb, J. R. Cheeseman, G. Scalmani, V. Barone, H. P. H. G. A. Petersson, H. Nakatsuji, M. Caricato, X. Li, M. H. A. F. Izmaylov, J. Bloino, G. Zheng, J. L. Sonnenberg, T. N. M. Ehara, K. Toyota, R. Fukuda, J. Hasegawa, M. Ishida, J. Y. Honda, O. Kitao, H. Nakai, T. Vreven, J. A. Montgomery, E. B. J. E. Peralta, F. Ogliaro, M. Bearpark, J. J. Heyd, J. N. K. N. Kudin, V. N. Staroverov, T. Keith, R. Kobayashi, J. T. K. Raghavachari, A. Rendell, J. C. Burant, S. S. Iyengar, J. B. C. M. Cossi, N. Rega, J. M. Millam, M. Klene, J. E. Knox, et al., 2010, Gaussian, Inc., Wallingford CT 7A. S. Dapprich, I. Komaromi, K. S. Byun, K. Morokuma, M. J. Frisch, *J. Mol. Struct. THEOCHEM* 1999, 461-462, 1-21.
8A. J.-D. Chai, M. Head-Gordon, *Phys. Chem. Chem. Phys.* 2008, 10, 6615.
9A. V. A. Rassolov, *J. Comput. Chem.* 2001, 22, 976-984.
10A. R. Ditchfield, W. J. Hehre, J. A. Pople, *J. Chem. Phys.* 1971, 54, 724-728.
11A. J. J. P. Stewart, *J. Mol. Model.* 2007, 13, 1173-1213.
12A. T. Lu, F. Chen, *J Comput Chem* 2012, 33, 580.
13A. G. A. Zhurko, D. A. Zhurko, n.d., Available at: http://www.chemcraft.prog.com, acces.
14A. U. Salzner, A. Aydin, *J. Chem. Theory Comput.* 2011, 7, 2568-2583.
15A. T. Tsuneda, J. W. Song, S. Suzuki, K. Hirao, *J. Chem. Phys.* 2010, 133, DOI 10.1063/1.3491272.
16A. D. D. Mendez-Hernandez, P. Tarakeshwar, D. Gust, T. A. Moore, A. L. Moore, V. Mujica, *J. Mol. Model.* 2013, 19, 2845-2848.
17A. H. Reiss, *J. Phys. Chem.* 1985, 89, 3783-3791.
18A. A. D. Becke, *J. Chem. Phys.* 1988, 88, 2547-2553.

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. It should also be understood that the appended drawings are not necessarily to scale, presenting a somewhat simplified representation of various features and basic principles of the invention.

What is claimed is:

1. A sensor comprising:
   a conductive region in electrical communication with at least three electrodes,
   the electrodes insulated and separated from each other with a dielectric layer having an adhesion layer thereon, the electrodes including source-drain electrodes, and
   the conductive region including a conductive material and an in situ activated redox-active selector comprising a metalloporphyrin, the metalloporphyrin immobilized with respect to a carbon nanotube in the conductive material by a ligand that is covalently bound to the carbon nanotube, the redox-active selector responsive to an applied gate voltage that transiently reduces the redox-active selector such that the in situ activated redox-active selector is configured to bind an analyte more readily in a first redox state compared to a second redox state, the sensor having a selectivity to ppm levels of carbon monoxide in air and being operational in air.

2. The sensor of claim 1, wherein the conductive material includes a carbon material.

3. The sensor of claim 2, wherein the carbon material includes amorphous carbon, graphene, graphite, a single walled carbon nanotube, and/or a multiwalled carbon nanotube.

4. The sensor of claim 1, wherein the conductive material includes a conductive polymer.

5. The sensor of claim 1, wherein the analyte is carbon monoxide.

6. The sensor of claim 5, wherein the metalloporphyrin is capable of forming a stable complex with the carbon monoxide.

7. The sensor of claim 1, wherein the metalloporphyrin includes iron.

8. The sensor of claim 1, wherein the ligand that is covalently bound to the carbon nanotube is bound to the metalloporphyrin.

9. The sensor of claim 1, wherein the ligand that is covalently bound to the carbon nanotube is a nitrogen-containing ligand.

10. The sensor of claim 1, wherein the ligand that is covalently bound to the carbon nanotube includes a pyridyl group.

11. The sensor of claim 1, wherein the redox-active selector includes an iron porphyrin complex and/or a triphenylmethyl compound.

12. The sensor of claim 1, wherein the three electrodes include a source electrode, a drain electrode and a gate electrode.

13. A method of sensing an analyte, comprising:
    exposing a sensor to a sample, the sensor including:
    a conductive region in electrical communication with at least three electrodes, the electrodes insulated and separated from each other with a dielectric layer having an adhesion layer thereon, the electrodes including source-drain electrodes,
    the conductive region including a conductive material and an in situ activated redox-active selector comprising a metalloporphyrin, the metalloporphyrin immobilized with respect to a carbon nanotube in the conductive material by a ligand that is covalently bound to the carbon nanotube, the redox-active selector responsive to an applied gate voltage that transiently reduces the redox-active selector such that the in situ activated redox-active selector is configured to bind an analyte in the sample more readily in a first redox state compared to a second redox state, the sensor having a selectivity to ppm levels of carbon monoxide in air and being operational in air; and
    measuring an electrical property at the electrodes.

14. The method of claim 13, wherein the sample is a gas.

15. The method of claim 13, wherein the conductive material includes a carbon material or a conducting polymer.

16. The method of claim 15, wherein the carbon material includes amorphous carbon, graphene, graphite, a single walled carbon nanotube, and/or a multiwalled carbon nanotube.

17. The method of claim 13, wherein the analyte is carbon monoxide or a sulfide.

18. The method of claim 17, wherein the metalloporphyrin is capable of forming a stable complex with the carbon monoxide.

19. The method of claim 13, further comprising applying a negative gate voltage.

20. A method of preparing a sensor comprising:
    forming a conductive region in electrical communication with at least three electrodes, the electrodes insulated and separated from each other with a dielectric layer having an adhesion layer thereon, the electrodes including source-drain electrodes,
    the conductive region including a conductive material and an in situ activated redox-active selector comprising a metalloporphyrin, the metalloporphyrin immobilized with respect to a carbon nanotube in the conductive material by a ligand that is covalently bound to the carbon nanotube, the redox-active selector responsive to an applied gate voltage that transiently reduces the redox-active selector such that the in situ activated redox-active selector is configured to bind an analyte more readily in a first redox state compared to a second redox state, the sensor having a selectivity to ppm levels of carbon monoxide in air and being operational in air.

\* \* \* \* \*